US010076261B2

(12) United States Patent
Arnone et al.

(10) Patent No.: US 10,076,261 B2
(45) Date of Patent: Sep. 18, 2018

(54) IMAGING APPARATUS AND METHOD

(75) Inventors: Donald Dominic Arnone, Cambridge (GB); Bryan Edward Cole, Cambridge (GB); Craig Michael Ciesla, Cambridge (GB)

(73) Assignee: TeraView Limited, Cambridge (GB)

( * ) Notice: Subject to any disclaimer, the term of this patent is extended or adjusted under 35 U.S.C. 154(b) by 795 days.

(21) Appl. No.: 10/220,717

(22) PCT Filed: Mar. 5, 2001

(86) PCT No.: PCT/GB01/00956
§ 371 (c)(1),
(2), (4) Date: Nov. 25, 2002

(87) PCT Pub. No.: WO01/65240
PCT Pub. Date: Sep. 7, 2001

(65) Prior Publication Data
US 2003/0149346 A1    Aug. 7, 2003

(30) Foreign Application Priority Data

Mar. 3, 2000 (GB) .................................. 0005225.8

(51) Int. Cl.
*G01N 21/35* (2014.01)
*G01N 21/31* (2006.01)
(Continued)

(52) U.S. Cl.
CPC .............. *A61B 5/05* (2013.01); *A61B 5/0507* (2013.01); *A61B 5/4547* (2013.01);
(Continued)

(58) Field of Classification Search
USPC ............... 600/473–478; 250/330, 340, 358.1
See application file for complete search history.

(56) References Cited

U.S. PATENT DOCUMENTS 4,891,581 A * 1/1990 Takiguchi ...................... 324/96
5,413,098 A * 5/1995 Benaron ....................... 600/310
(Continued)

FOREIGN PATENT DOCUMENTS

EP    0 828 143 A2    3/1998
EP    0 828 162 A2    3/1998
(Continued)

OTHER PUBLICATIONS

D.M. Mittleman, et al., "T-Ray Imaging", *IEEE Journal of Selected Topics in Quantum Electronics*, U.S., IEEE Service Center, vol. 2, No. 3, Sep. 1, 1996, pp. 679-692, ISSN: 11077-260X.
(Continued)

*Primary Examiner* — Patricia Park
(74) *Attorney, Agent, or Firm* — Blank Rome LLP

(57) ABSTRACT

A range of technique for investigating a sample such as obtaining images and/or spectral information are described. The techniques include a method for deriving structural information about a sample as a continuous function of the depth below the surface of the sample, a method for evaluating a part of the structure of a sample located between two interfaces within the sample, and a contrast enhancing method and apparatus which has a quick image acquisition time.

7 Claims, 22 Drawing Sheets

(51) Int. Cl.
  *A61B 5/05*    (2006.01)
  *A61B 5/00*    (2006.01)
  *G01N 21/3581* (2014.01)
  *G01N 21/47*   (2006.01)
  *G01N 21/43*   (2006.01)

(52) U.S. Cl.
  CPC ..... *G01N 21/3581* (2013.01); *G01N 21/4795* (2013.01); *G01N 21/43* (2013.01)

(56) References Cited

U.S. PATENT DOCUMENTS

| | | | | |
|---|---|---|---|---|
| 5,623,145 | A | * | 4/1997 | Nuss .............................. 250/330 |
| 5,710,430 | A | | 1/1998 | Nuss |
| 5,789,750 | A | * | 8/1998 | Nuss .......................... 250/338.1 |
| 5,939,721 | A | * | 8/1999 | Jacobsen ............... G01J 3/2823 250/330 |
| 6,078,047 | A | * | 6/2000 | Mittleman et al. ......... 250/338.1 |
| 6,208,886 | B1 | * | 3/2001 | Alfano ................. A61B 5/0073 250/341.1 |
| 6,356,349 | B1 | * | 3/2002 | Koehl et al. ................... 356/432 |
| 6,849,852 | B2 | * | 2/2005 | Williamson ............... 250/341.6 |

FOREIGN PATENT DOCUMENTS

| | | |
|---|---|---|
| EP | 0 864 857 A1 | 9/1998 |
| EP | 0864857 | 9/1998 |
| WO | 0075641 | 12/2000 |

OTHER PUBLICATIONS

C.M. Ciesla et al., "Biomedical Applications of Terahertz Pulse Imaging", Proc. Spie; Conference; Commercial and Biomedical Application of Ultrafast Lasers II; San Jose; 24.-25.01.200, vol. 3934, 2000, pp. 73-81.

* cited by examiner

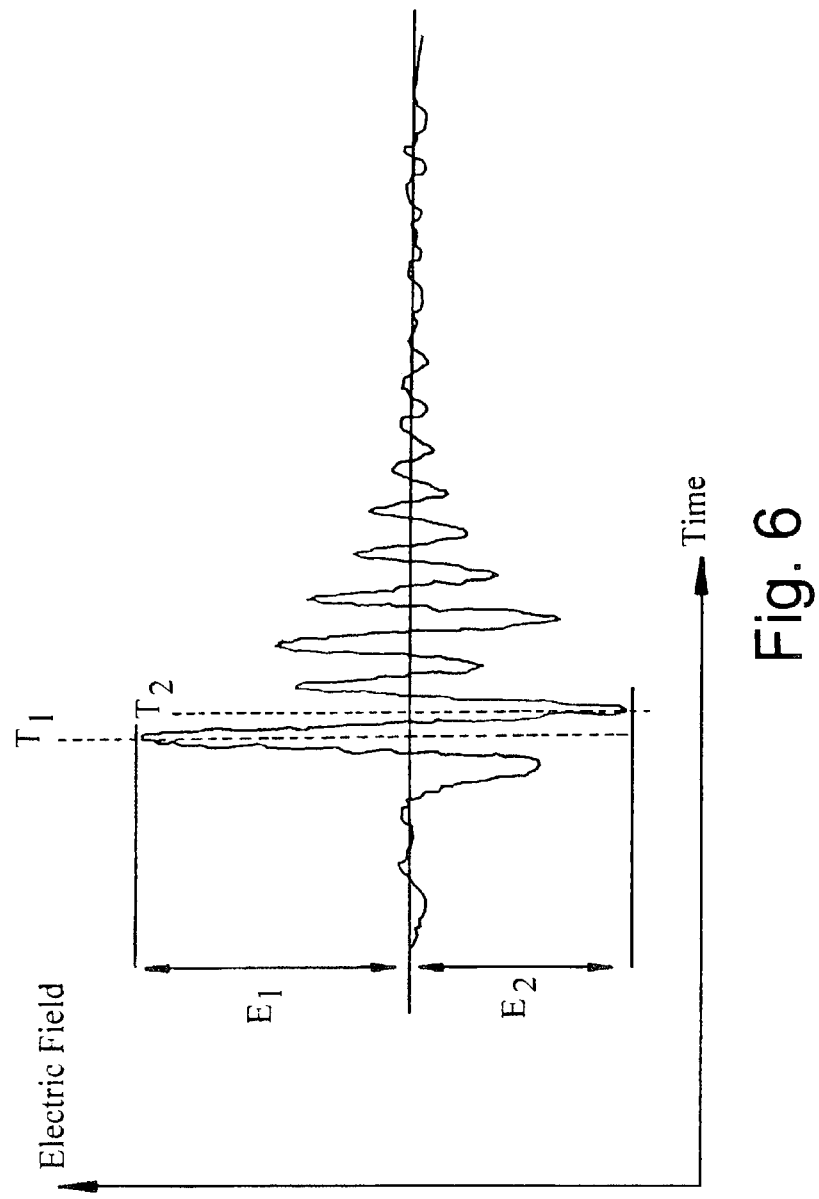

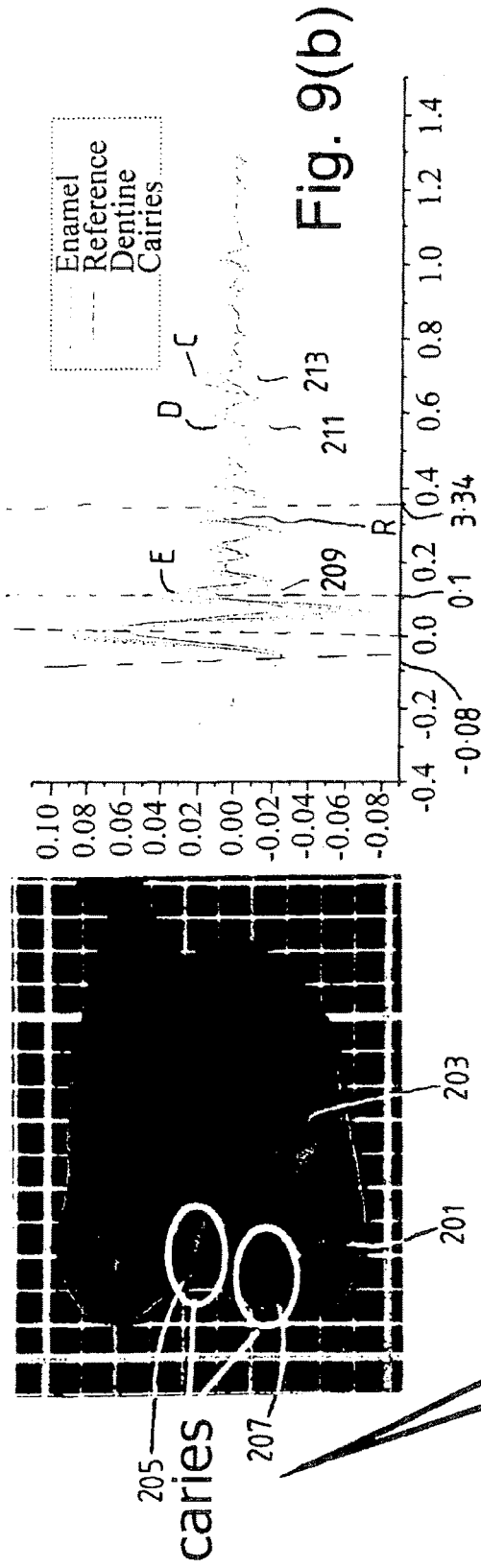
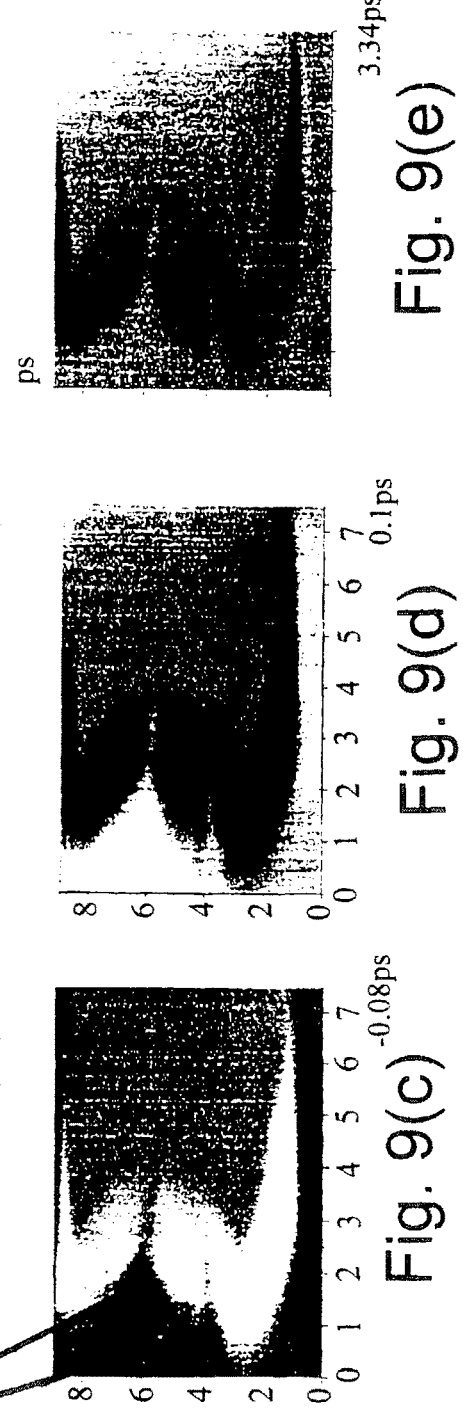
Fig. 9(a) Fig. 9(b) Fig. 9(c) Fig. 9(d) Fig. 9(e)

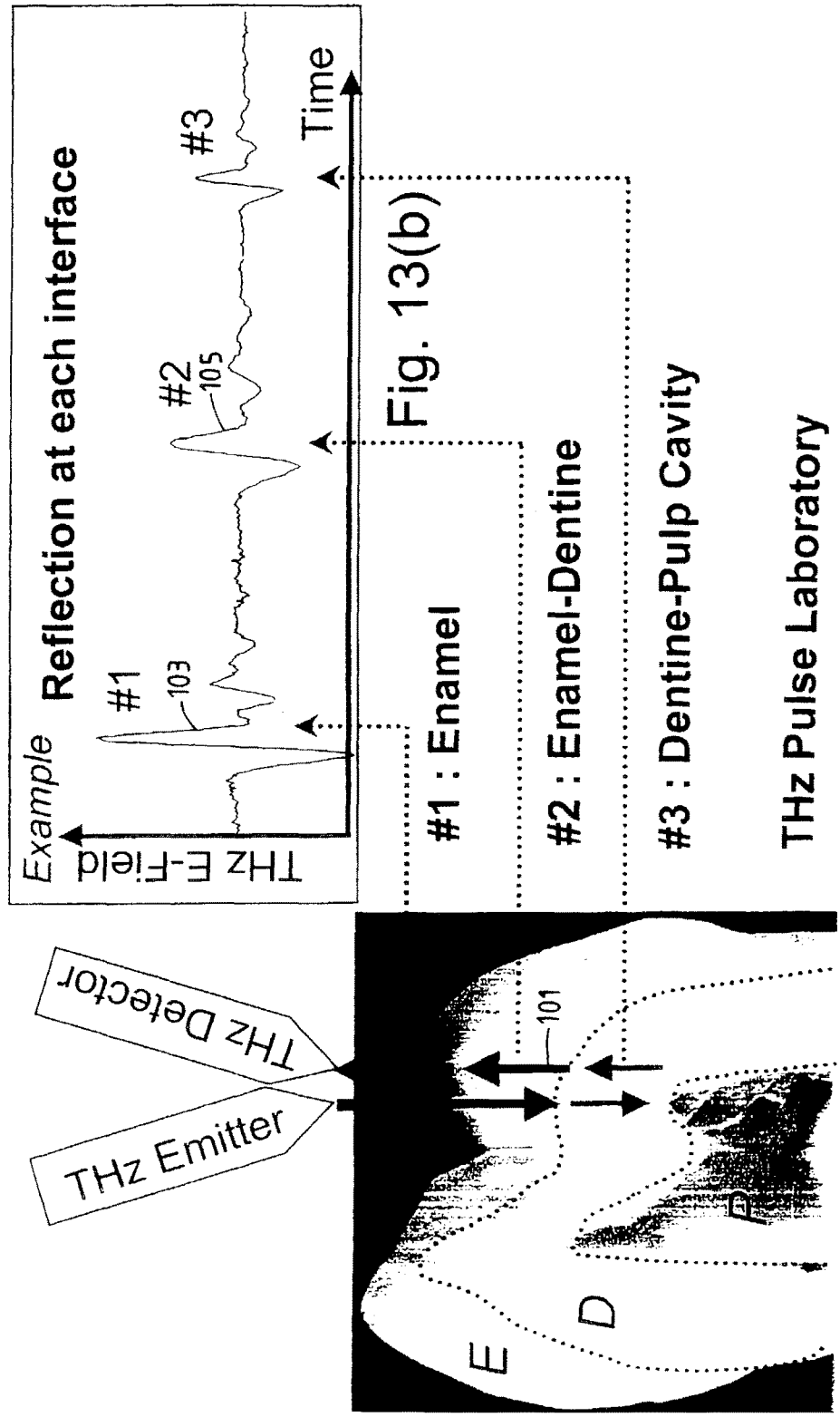

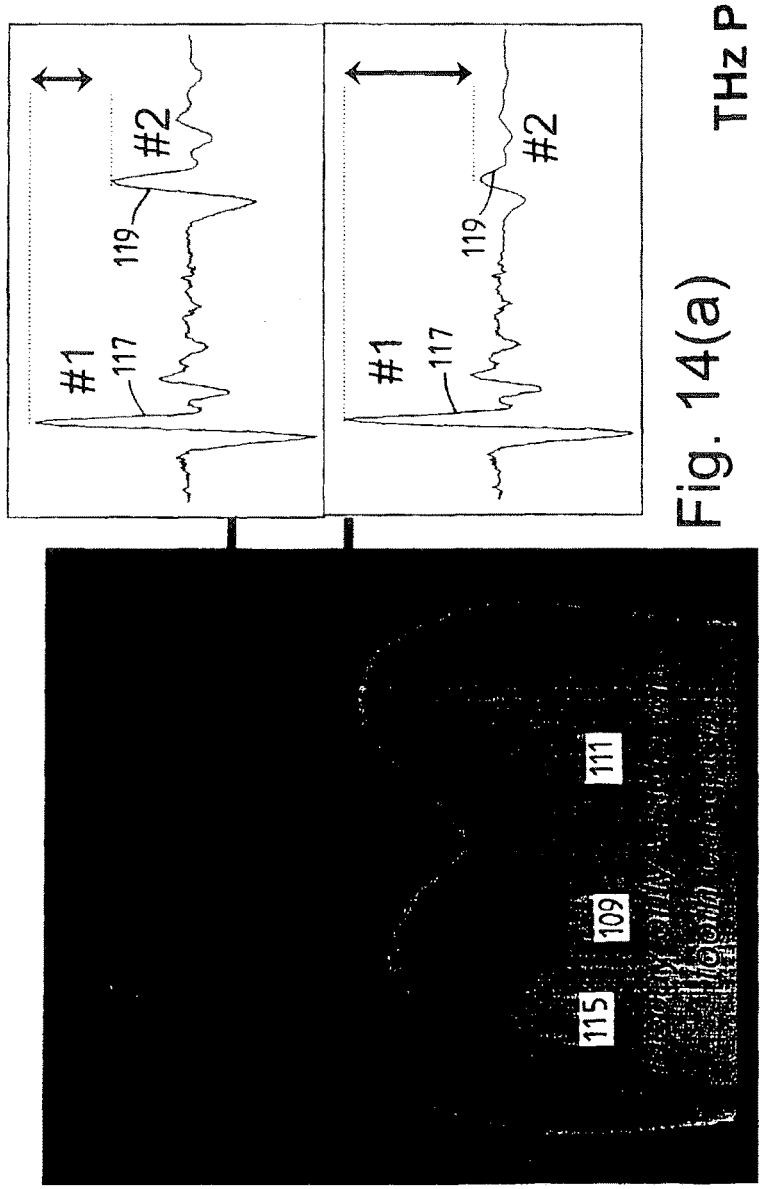

IMAGING APPARATUS AND METHOD

The present invention is concerned with the field of investigating and imaging samples primarily using radiation in the frequency range from 25 GHz to 100 THz. This frequency range extends from the mid infrared range up to, and including the lower end of the microwave range. This range of frequencies encompasses the Terahertz (THz) range and is generally referred to as THz radiation.

Such radiation is non-ionising and, as a result, it is particularly of use in medical applications. In any type of medical imaging, radiation is generally reflected from or transmitted through the patient. Radiation in the above frequency range is generally quite heavily absorbed in structures having a high water content. Therefore, reflection measurements are believed to be of particular use in such investigations.

Reflection measurements in non-lossy materials have been previously demonstrated in EP 0 864 857. This document explains how to perform simple analysis using reflection measurements on non-lossy materials which have sharp discontinuities in their refractive index. The position of the dielectric interfaces within a floppy disc is used to demonstrate the technique.

However, medical samples in general are particularly lossy media, in other words, Terahertz radiation is strongly absorbed in such structures. Also, there is a need to be able to determine the structure of sample which does not have sharp discontinuities in its refractive index.

The present invention seeks to address the above problems, and in a first aspect, provides a method of imaging a sample, the method comprising the steps of:
  irradiating a surface of a sample with pulse of electromagnetic radiation, said pulse having a plurality of frequencies in the range from 25 GHz to 100 THz;
  detecting said radiation reflected from the sample and deriving information about the structure of the sample as a function of depth from the surface of the sample The above method is ideally intended for use with biological samples. Also, the above method derives information as a continuous function of the depth from the surface of the sample. Preferably either the refractive index or the absorption coefficient is derived as a function of depth from the surface of the sample. The structural information can be derived as a continuous analytical function of the measured reflected radiation.

Preferably, the method further comprises the step of obtaining a reference signal. The said reference signal is preferably a signal taken without the presence of the sample and is preferably obtained by reflecting the radiation off a mirror which has substantially perfectly reflecting.

The above method uses reflections from the sample in order to obtain information about the continuously changing absorption coefficient, refractive index and other structural parameters of the sample. The technique does not rely on the present of sharp discontinuities within the sample to derive information about specific regions of the sample, because the method provides an analytical technique for deriving a continuously changing parameter as a function of depth.

It is possible to perform this analysis using the above method as the wavevector of each frequency component of the THz pulse is dominated by the absorption coefficient as opposed to the refractive index (which is the case for lossless media). Preferably the frequency range from 50 GHz to 80 THz is used, more preferably from 100 GHz to 50 THz.

In a second aspect, the present invention provides an apparatus for investigating a sample, the apparatus comprising:
  means for irradiating a surface of a sample with a pulse of electromagnetic radiation, said pulse having a plurality of frequencies in the range from 25 GHz to 100 THz;
  means for detecting said radiation reflected from the sample and deriving structural information about the sample as a function of depth from the surface of the sample.

Of course, it is possible to study samples which have sharp discontinuities in the refractive index using the above method. In both lossless and lossy media, the signal due to reflection from a discontinuity in the refractive index such as an internal dielectric interface or an external surface of the sample can be easily detected. Such a signal usually manifests itself in terms of a large peak in the reflected radiation which can be easily detected.

This reflection data can be used to determine the position of interfaces within the same. However, it can also be used to obtain data concerning the absorption of the sample between the two interfaces. Comparing the signals from different interfaces in different parts of the sample, is particularly of use in studying samples where there is some variation in the absorption of the latter between the two interfaces.

Therefore, in a third aspect, the present invention provides a method for studying a sample, the method comprising the steps of:
  irradiating a first part and a second part of a surface of the sample with electromagnetic radiation having a frequency in the range from 25 GHz to 100 THz, the first interface being located closer to the surface than the second interface;
  detecting the signal due to reflection of the radiation from the first and second interfaces of the two parts of the sample; and
  comparing the peak height of the signal from the second interface with that from the first interface to produce a connected second interface signal and comparing the connected second interface signals.

The step of comparing the signal from the first interface with that of the second could comprise the step of dividing the peak height of the signal from the second interface with that from the first or subtracting the signals. Alternatively, the method could comprise the step of comparing the two signals from the two different parts of the sample with respect to the peak height.

Comparing the peak heights of the signal from the first and second interfaces allows any variations in detected radiation due to differences in the sample position and differences in the sample which are not between the first and second interfaces to be taken into account.

The above method is particularly of use when looking for an abnormality in a sample. For example, looking for a skin tumour. In such a sample, there will be a reflection from an interface above the tumour such as the external surface of the skin, there will also be a reflection from an interface below the skin, for example, the skin/fat interface. A tumour has been shown to absorb THz quite strongly. Therefore, the signal from the second interface will be weaker in a tumourous region than in a non tumourous region.

Hence, one of the parts of the sample is preferably a healthy part which is used as a reference.

Further, by scanning the THz beam across the skin while looking at the relative height of the signal from the second interface with respect to the first, it is possible to build up a picture of the extent of the tumour.

The above method is not only limited to looking for tumours. It has been shown that areas of teeth which have been subjected to dental caries are also more strongly absorbing than healthy areas of the teeth. Therefore, there will be a marked change in the signal from the second interface from the healthy region of the teeth to the carious region of the teeth.

The above method may comprise the step of looking at many different parts of the sample, and generating a plot of the corrected second peak against the position on the sample. An image of the sample could also be built up by plotting the corrected second peak against the position on the sample.

To build up a 2D image, an area of the sample is subdivided into pixels and the reflected radiation form each of the pixels is detected.

The radiation used can be pulsed radiation which comprises a plurality of frequencies or even continuous wave radiation which has substantially a single frequency.

In a fourth aspect, the present invention provides an apparatus for generating an image of a sample, the apparatus comprising:
    means for irradiating a sample with a pulse of electromagnetic radiation, said pulse having a plurality of frequencies in the range from 25 GHz to 100 THz;
    means for detecting the amplitude of the radiation reflected from or transmitted by the sample; and
    means for generating an image of sample using the amplitude of the radiation detected at a single point in time.

When studying a sample, it is usually desirable to generate and image of the sample. Typically, images of the sample have been generated by plotting the maxima or minima of the detected Terahertz radiation. However, it has been found that a better contrast can be obtained by looking at the THz electric field for a particular time delay.

Therefore, in a fifth aspect, the present invention provides a method of imaging a sample, the method comprising the steps of:
    irradiating a sample with a pulse of electromagnetic radiation, said pulse having a plurality of frequencies in the range from 25 GHz to 100 THz;
    detecting the amplitude of the radiation; and
    generating an image of sample using the amplitude of the detected radiation at a particular point in time.

In order to generate an image, it is necessary to measure the THz signal from a number of different parts of the sample. Typically, the area of the sample which is to be imaged will be subdivided into a two-dimensional array of pixels and the radiation will be detected from each of the pixels. In order to detect radiation from each of the pixels, the sample may be moved relative to the beam of radiation or the beam may be moved relative to the sample, or both. Alternatively, the whole area of the sample could be irradiated and the radiation transmitted through or detected form the area of the sample could be detected by a CCD camera or the like.

The Terahertz pulse which is used to irradiate the sample will spread out due to its passage through the sample. As a result, different parts of the pulse will be detected at different times. The leading edge of the pulse of a particular features of the pulse, can be thought of as arriving at the detector at a time t=0, then the other parts of the pulse will arrive at the detector with a delay time "t".

The method of the fifth aspect of the present invention generates an image using a specific 't'.

The radiation can be detected at a specific time 't', this is advantageous as it does not require detecting radiation for every 't' and hence the acquisition time of the image is substantially improved.

Alternatively, it may be desirable to detect the radiation for a range of 't' and then select a particular "t" in order to generate the image. This allows an image to be scannable using "t" as the scanning variable. Thus, someone using the method could scan the image for various "t" until the image with the best contrast was obtained.

This method could be used for either or both of transmitted data or reflected data.

In a sixth aspect, the present invention provides an apparatus for imaging a sample comprising:
    means for irradiating a sample with a pulse of electromagnetic radiation, said pulse having a plurality of frequencies in the range from 25 GHz to 100 THz;
    means for detecting the amplitude of the radiation reflected from or transmitted by the sample; and
    means for generating an image of sample using the amplitude of the radiation detected at a single point in time.

The apparatus preferably further comprising means for displaying a plurality of images generated from different time points. More preferably, the apparatus comprises optimising means for optimising the image using the variable parameter of the delay time.

The present invention will now be described with reference to following preferred non-limiting embodiments:

FIG. 6 shows a schematic trace of a pulse detected by the imaging system of FIG. 1;

FIG. 9a shows a visible image of a slice through a tooth, FIG. 9b shows a typical THz time domain trace for a tooth, FIGS. 9c, d and e show time slice images for the tooth at delayed times −0.08 ps, 0.1 ps and 3.34 ps;

FIG. 10a to 10d show four images of time slices through the tooth shown in FIG. 9a;

FIG. 13 shows a visible image of a tooth and a THz signal from the tooth;

FIG. 14 shows a visible image of a tooth and two THz traces of diseased and healthy parts of the tooth;

Figure 20:
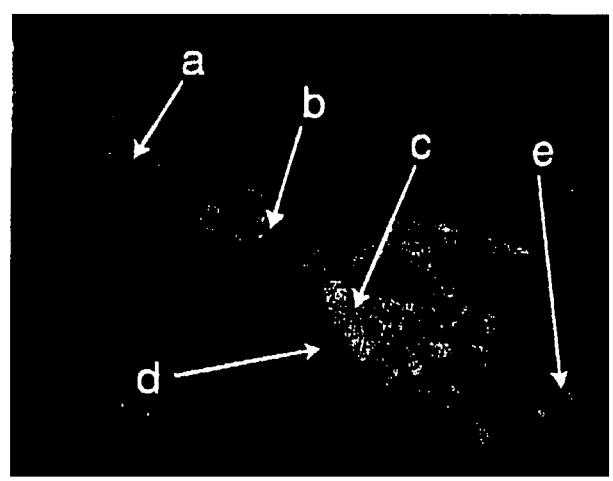
FIG. 20 is a visible image of a human arm and hand indicating points on the arm and hand which are measured to produce the results in the following figures.
Figure 24A:
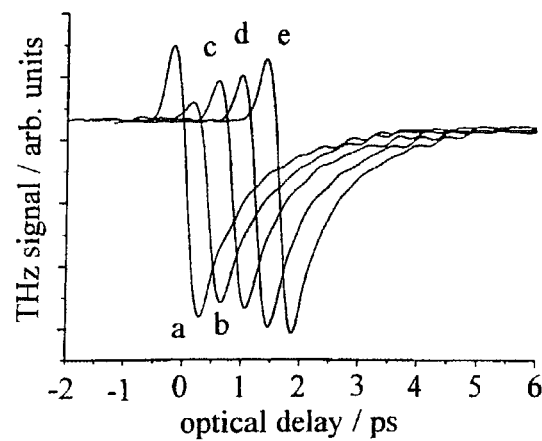
Figure 24B:
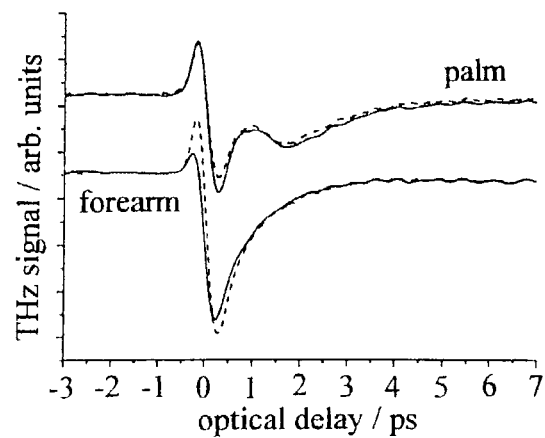
Figure 25A:
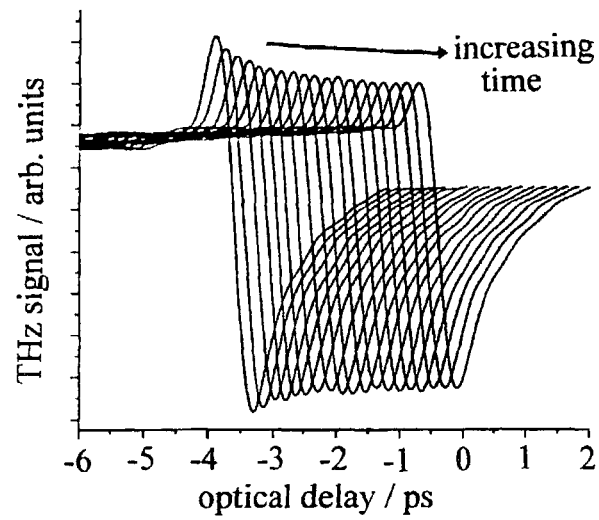
Figure 25B:
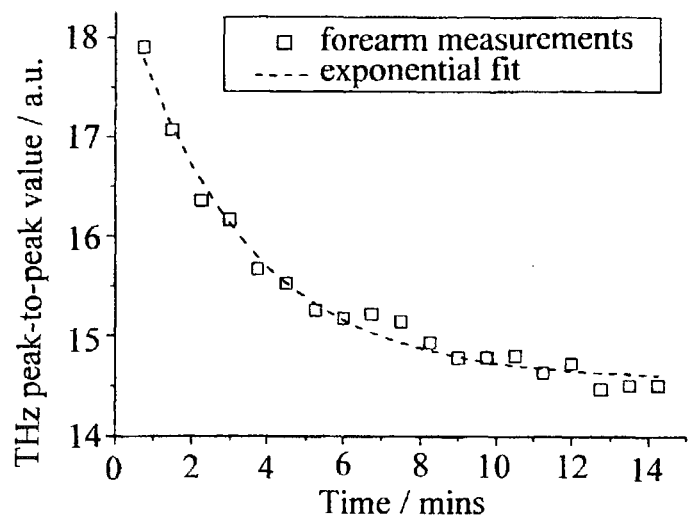

FIG. 24a is a comparative plot of a THz measurement of the forearm of FIG. 20 under different wetting conditions; and FIG. 24b shows plots of measurements of the palm and forearm before and after application of glycerine solution; and FIG. 25a is a comparative plot of the changing characteristics of a forearm over a 15 minute period, and FIG. 25b is a plot of the maximas of the traces of FIG. 25a against time.

Figure 1:
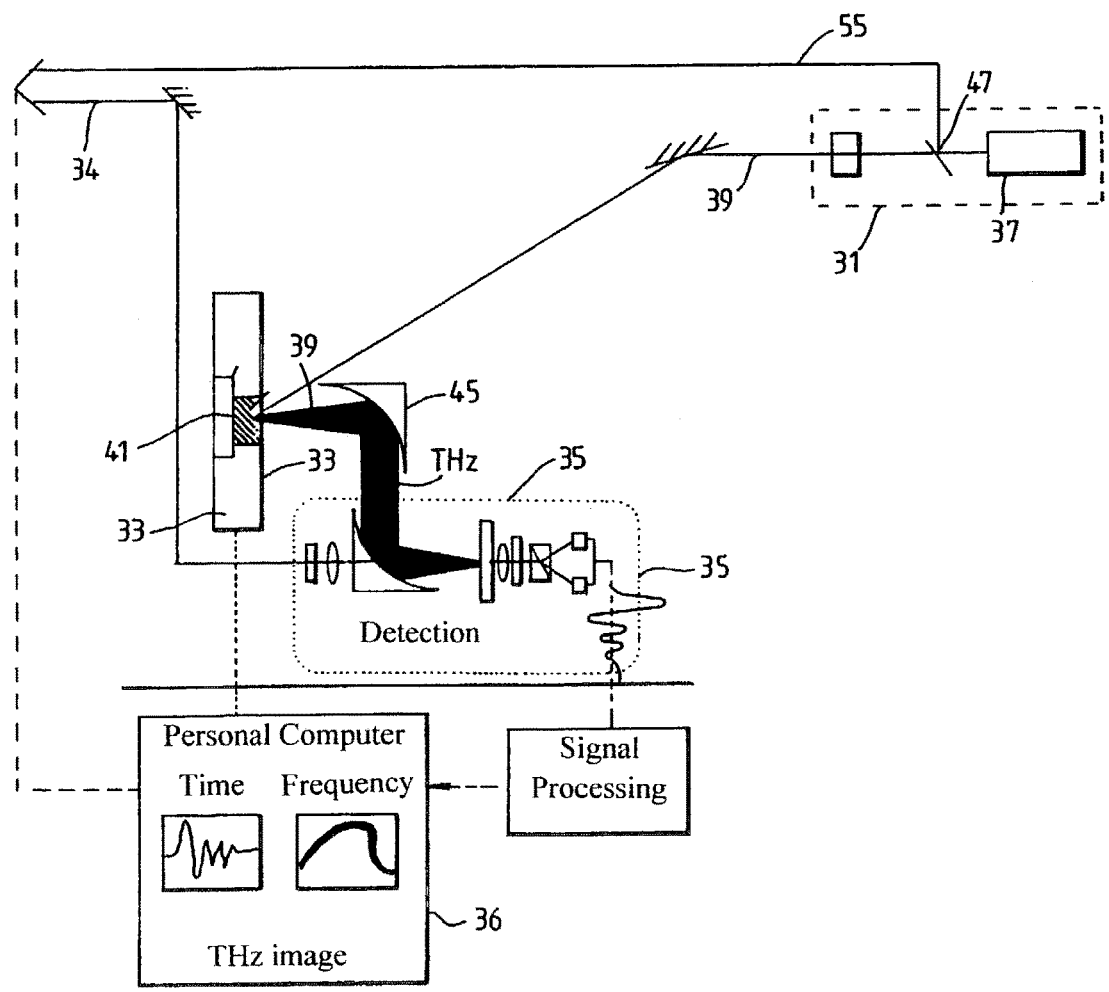
FIG. 1 shows a schematic imaging system in accordance with an embodiment of the present invention.

FIG. 1 shows a basic THz imaging system. The system can be simplified into three main sections, a generator 31, an imaging section 33 and a detection section 35. THz radiation is generated in the generating section 31 by using a THz emitter which is supplied by a visible pulsed laser 37.

A THz beam 39 is emitted from generation section 31 and is directed onto sample 41 of the imaging section 33. The THz beam 39 is then reflected from sample 41 and directed via further optics 45 into the detection section 35. The THz beam which is reflected from the sample 41 is beam 39.

The detection section reads the information carried in the detected THz signal via a visible light signal and AC Pockels effect. The visible light can be obtained from laser 37 via beam splitter 47. Laser 37 is a Ti:Sapphire laser which typically produces wavelengths in the range of 900 nm to 350 nm, with a pulse width of 50 fs and a repetition rate of 82 MHz.

Beam splitter 47 splits the beam into a reference beam 55 and a beam for THz generation. A time delay is added to the reference beam 55 via time delay line 34. Varying the time delay via the time delay line allows the phase of the reference beam to be varied with respect to that of the THz beam 39. This is used in detecting the THz beam in detection system 35. The system (e.g. the control of the sample 41 movement, the time delay 34 and the detected signal processing) is controlled by computer 36. Details of the AC Pockels effect will be described with reference to FIG. 3.

Figure 2:
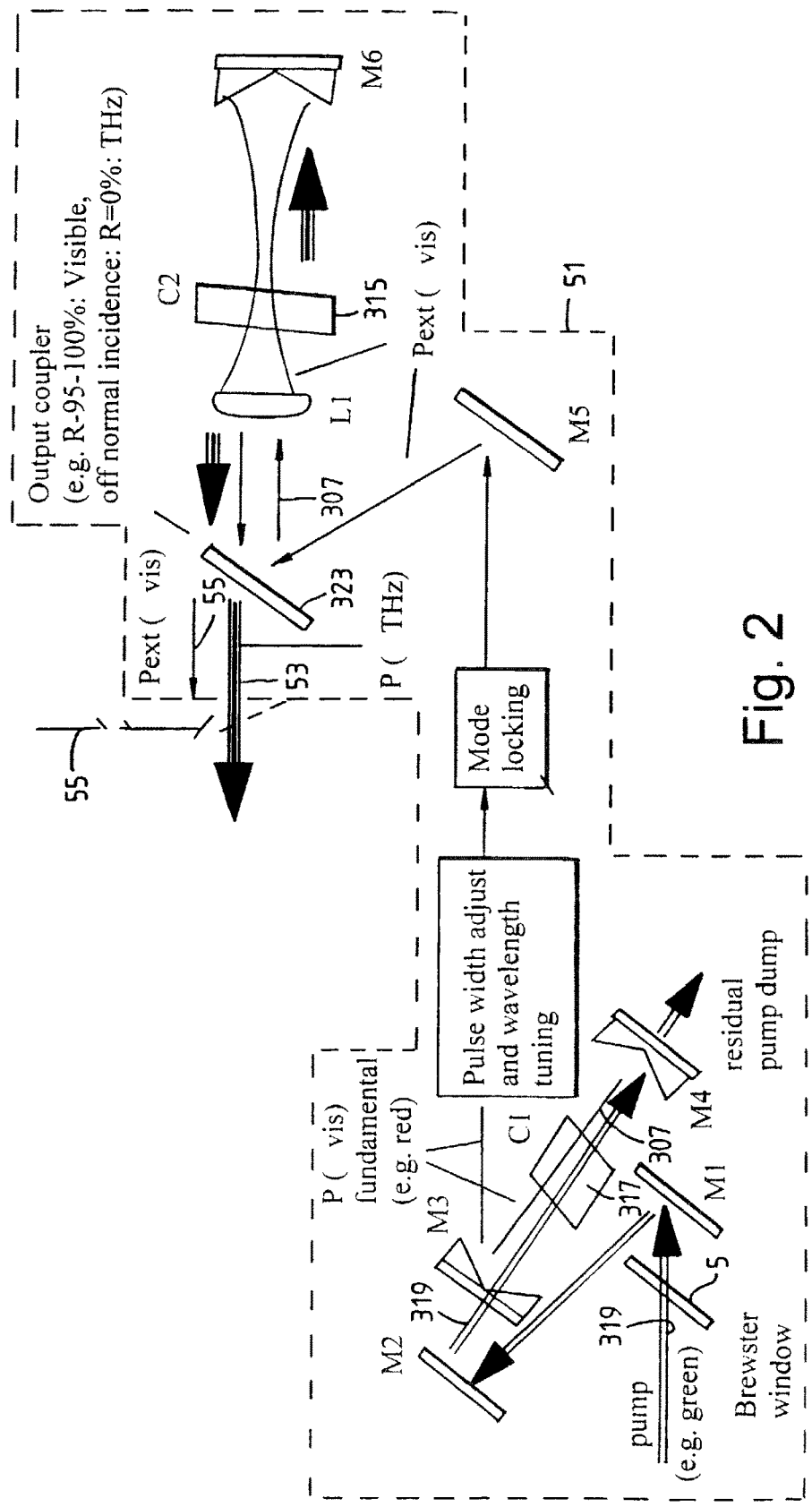
FIG. 2 shows an example of a generation section for use with the imaging system of FIG. 1.

FIG. 2 shows a generator which can be used with the imaging system of FIG. 1 Here, for simplicity, details of the detection part of the system will be omitted. These will be described with reference to FIG. 3.

FIG. 2 shows a THz generator using a frequency conversion member which may be a crystal which non-linear properties of the like such as ZnTe. The radiation used to generate the THz radiation via frequency conversion member 315. Radiation is supplied to frequency conversion member 315 from Ti:Sapphire crystal 317. Ti:Sapphire crystal 317 emits a pump beam, which comprises pulses of radiation, in response to radiation with laser driving beam 319. In order to provide efficient lasing, it is desirable to continually reflect the pump beam 307 onto Ti:Sapphire crystal 317. Therefore, the lasing crystal 317 is typically provided within a lasing cavity.

The driving beam 319 is directed onto crystal 317 using mirrors M1 and M2. The driving beam 319 can pass through mirror M3 and onto lasing crystal 317. The driving beam 319 which is not absorbed by crystal 317, is emitted through mirror M4. Mirror M4 serves to reflect any radiation back onto the lasing crystal 317. This radiation is then reflected via mirror M3 onto mirror M5 and onto output coupler 321. Output coupler 321 serves to reflect the pump beam 307 onto the frequency conversion member 315 to produce Terahertz radiation. The pump beam is focused onto frequency conversion member 315 via lens L1. Any radiation which is transmitted through the frequency conversion member 315 is reflected back through the frequency conversion member 315 by mirror M6. This radiation then impinges on output coupler 321.

Output coupler 321 transmits terahertz radiation, but it reflects most of the pump beam back onto mirror M5, which in turn reflects the radiation back onto the lasing crystal 317 via mirror M3. In other words, the lasing crystal 317 and the frequency conversion member 315 are all located within the same lasing cavity defined by mirror M6, the output coupler and mirrors M5, M3 and M4. The pump beam 307 is continuously reflected within this cavity to efficiently generate the pump beam and the THz beam.

The THz beam 53 which is emitted from output coupler 321 is directed into the imaging section 33 and onto sample 41 via THz imaging optics (not shown). The sample 41 is located on a motorised X-Y translation stage (not shown) so that the whole sample 41 can be imaged. (The x-y plane is orthogonal to the beam axis). The THz radiation carrying the imaging information from the sample is reflected into the THz detection system 35 via THz imaging optics 45.

Output coupler 321 transmits some visible radiation 55 as well as THz radiation as a reference beam 55. Imaging and electro-optic detection can be performed inside a single nitrogen-purged unit.

The sample 41 is mounted on a X-Y motorised translation stage (not shown) which is controlled by a PC computer (not shown). Each section (pixel) of the object may then be imaged. To improve the spatial resolution of the technique, off-axis parabolic mirrors, condenser cones, and lenses may be used to focus the beam to a diffraction limit spot. By mounting the sample in the near field of a condenser cone, the diffraction limit may be overcome and spatial resolution of about 50 µm may be achieved. The imaging system can function with or without such objects depending on the nature of the object to be imaged and the nature of the detection circuit.

Figure 3:
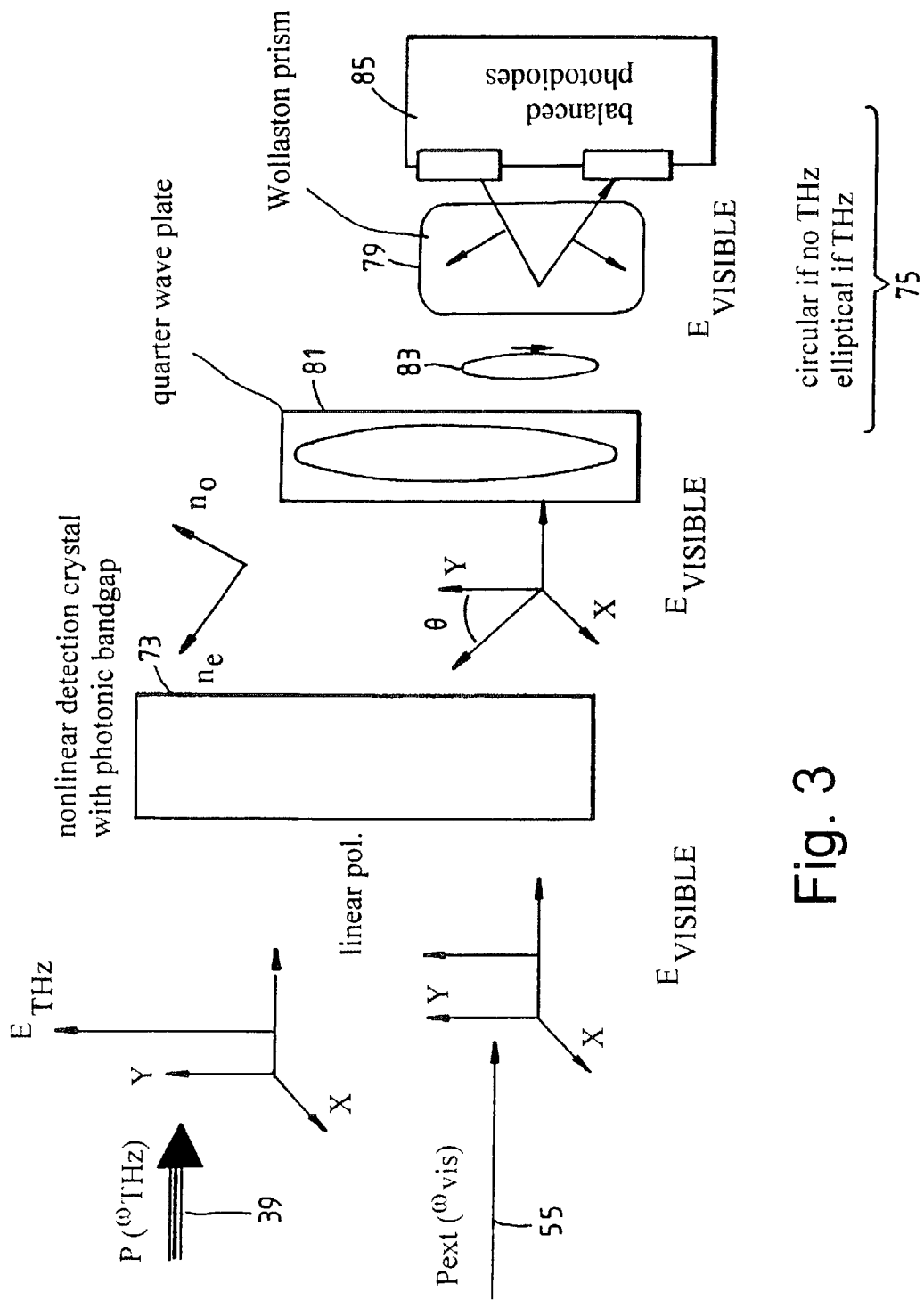
FIG. 3 shows an example of a detection section for use with the imaging system of FIG. 1.

FIG. 3 shows the detection system in detail. The THz beam 39 carrying the imaging information and a visible light beam 55 are inputted into the THz detection system. The visible light beam 55 acts as a reference beam which is incident on the detection crystal 73. The reference beam 55 is linearly polarised and the polarisation is orientated such that it has components along both the ordinary and extraordinary axis of the detection crystal 73. Each of the axes has distinct refractive indices $n_o$ and $n_e$ along the ordinary and extraordinary axis of the crystal 73 respectively. In the absence of a second (THz) radiation beam 39, the linearly polarised reference beam 55 passes through the detection crystal 73 with negligible change in its polarisation.

The applicant wishes to clarify that the angle Θ through which the polarisation is rotated by is negligible. However, the linearly polarised beam can become slightly elliptical. This effect is compensated for by a variable retardation waveplate, e.g. a quarter waveplate 81.

The emitted beam 77 is converted into a circularly polarised beam 83 using quarter wave plate 81. This is then split into two linearly polarised beams by a Wollaston Prism 79 (or equivalent device for separating orthogonal polarisation components) which directs the two orthogonal components of the polarised beam onto a balanced photodiode 85. The balanced photodiode signal is adjusted using wave plate 81 such that the difference in outputs between the two diodes is zero.

However, if the detector 73 also detects a secondary beam 69 (in this case a beam with a frequency in the THz range) as well as a reference beam, the angle Θ through which the polarisation is rotated by is not negligible. This is because the THz electric field modifies the refractive index of the visible (fundamental) radiation along one of the axes $n_e$, $n_o$. This results in the visible field after the detector 73 being elliptical and hence the polarisation components separated by the prism 79 are not equal. The difference in the voltage between the output diodes gives a detection voltage.

The reference beam 55 and the THz beam 39 should stay in phase as they pass through the crystal 73. Otherwise the polarisation rotation Θ is obscured. Therefore, the detection crystal 73 has phase matching means to produce a clear signal.

Figure 4:
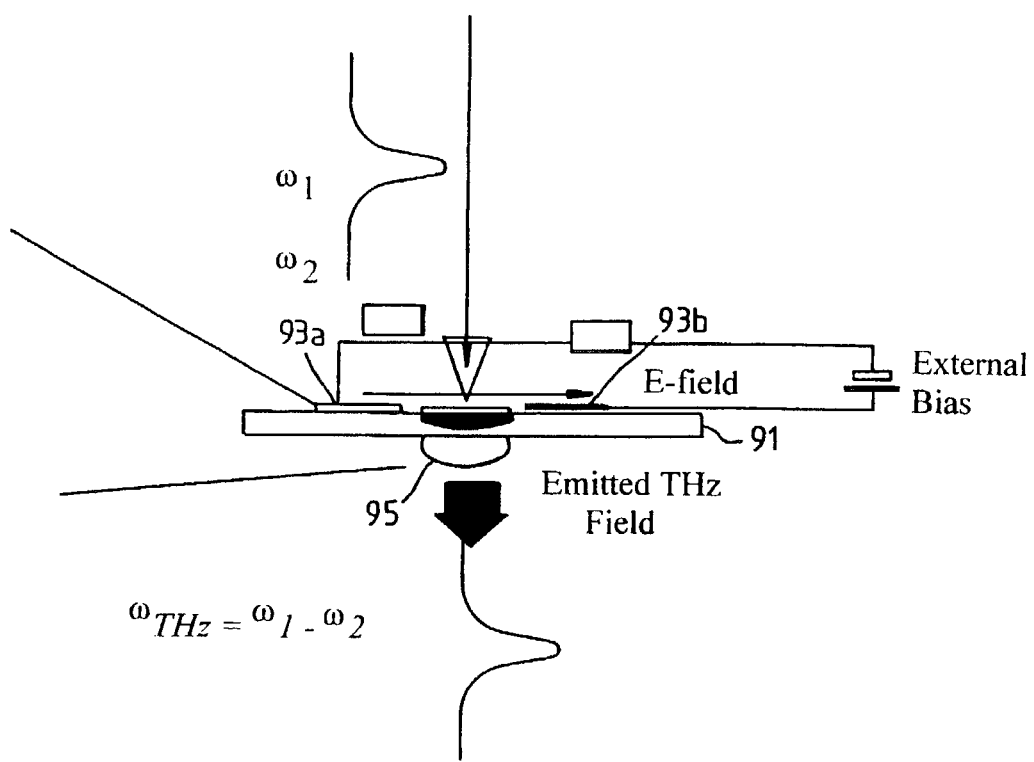
FIG. 4 shows a further example of a generator for use with the imaging system of FIG. 1.

Other types of generator may also be used. FIG. 4 illustrates a so-called photoconductive emitter. The emitter comprises a member 91 comprising a semiconductor such as low temperature GaAs, GaAs, Si on Sapphire etc. The semiconductor member has a pair of electrodes 93a and 93b located on its surface. The electrodes 93a and 93b are connected to a power supply such that a field can be generated between the two electrodes 93a and 93b.

The simplest electrode arrangement is show in FIG. 4. However, the electrodes may be triangular and arranged in a bow-tie shape, a so-called bow-tie antenna or they may be interdigitated electrodes at the centre of a bow tie or spiral antenna. Alternatively, such designs may be incorporated into transmission lines on the chip.

The semiconductor member is irradiated by a pump beam which is a pulse of radiation (about 70 fs) of the type which can be emitted by laser 37. The pulse comprises at least two frequencies $\omega_1$ and $\omega_2$, the difference of which gives a frequency in the THz regime. The pump beam impinges on the semiconductor member 91 on the part of its surface between the electrodes 93a and 93b, i.e. where the field is applied. The beating of the two visible or near-infrared frequencies in the non-linear region of the semiconductor member between the two electrodes 93a and 93b results in the emission of THz radiation from the semiconductor member 91. The semiconductor member 23 is provided with a lens 95, which may be of a hemispherical or other design, on its surface which is opposite to that of the surface with the electrodes, to allow the emission of a beam of THz radiation.

Figure 5:
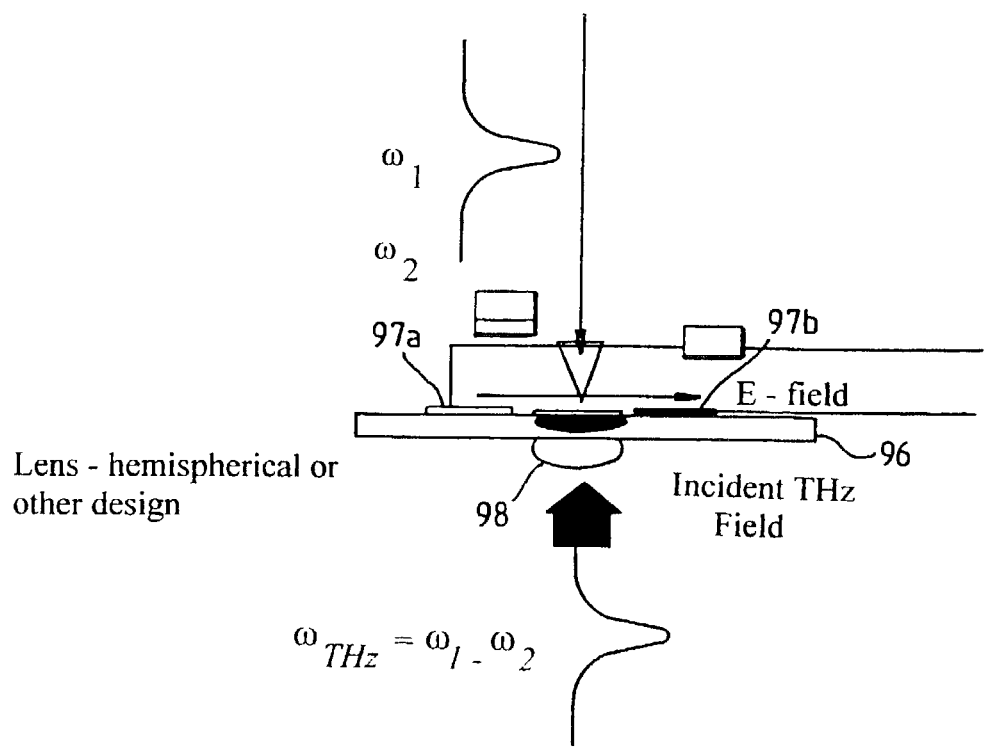
FIG. 5 shows a further example of a detector for use with the imaging system of FIG. 1.

FIG. 5 shows a further example of a detector which may be used with the imaging system of FIG. 1. This type of detector is known as a photoconductive detector and comprises a detection member which may be, for example, GaAs, Si on Sapphire etc. The THz radiation is incident on the back surface of the detection member 96. The radiation is collected by lens 98 which may be hemispherical or have another shape. On the opposing side of the detection member 96 is located a pair of electrodes 97a and 97b. The region between these two electrodes 97a and 97b is illuminated by radiation of the visible or near infrared range.

The near-infrared/visible radiation illuminates the surface of the detector between the electrodes 97a and 97b. The Terahertz radiation which is collected by lens 98 induces a photocurrent through the region between the electrodes 97a and 97b which is being illuminated by the visible/infrared radiation. The current which can be detected by the electrodes is proportional to the strength of the THz field.

The electrode 97a, 97b may be of a simple diode formation embedded in a transmission line. Alternatively, they may be triangular and arranged in the shape of a bow-tie to from a so-called bow-tie antenna. They may also be interdigitated electrodes at the centre of a bow-tie or spiral antenna.

FIG. 6 shows a schematic trace of a THz pulse which has been reflected from the sample using the type of apparatus which is shown for the example in FIG. 1.

An oscillating electric field is plotted on the y axis against time along the x-axis. Typically, methods of extracting information from the trace have used either the position in time of the maxima of the electric field ($T_1$) or the position in time of the minima of the electric field ($T_2$).

As it can be seen from FIG. 6, the magnitude of the measured electric field changes considerably with time. There is only a small time difference between $T_1$ and $T_2$. When looking at an area of the sample, a trace like the one shown in FIG. 6 will be obtained for each point of the sample. The trace will change from point to point or pixel to pixel dependent on the composition of the sample.

Figures 7A, 7B:
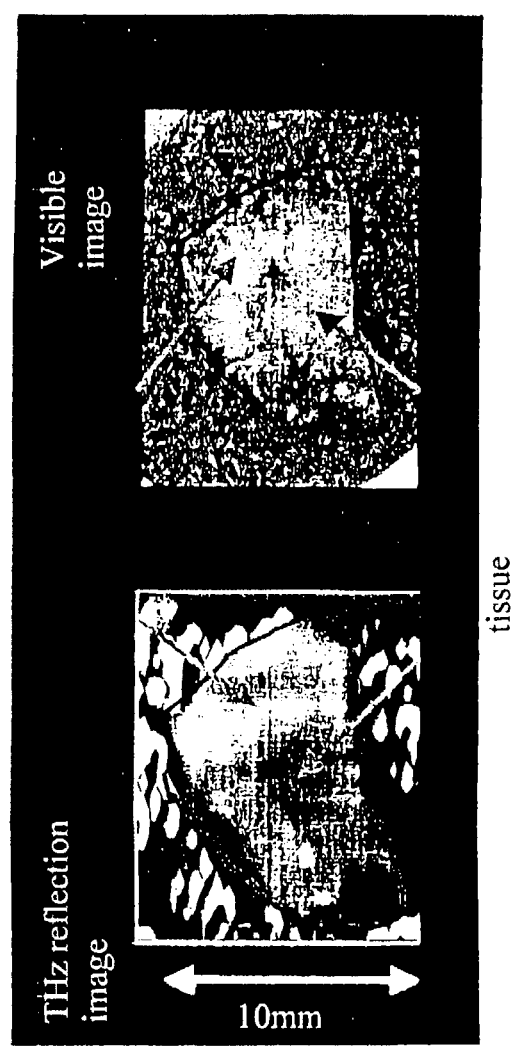
FIG. 7 shows an image of a skin carcinoma produced in accordance with an embodiment of the present invention.

FIG. 7 shows a reflection image of a skin carcinoma. FIG. 7a shows the THz image and FIG. 7b shows the image using visible radiation.

To generate the image in FIG. 7a, only reflected radiation from a single delay time i.e. a single point on the x axis of FIG. 6, is plotted. The delay time may be the maxima of the electric field in some parts of the sample or the minima of the electric field in other parts of the sample. It can be seen that this image shows good contrast. As it is only necessary to measure the THz signal at a particular delay time, there is no need to continually sample the whole of the THz pulse. Therefore, the image can be produced using a much shorter acquisition time. Also, the image requires less processing.

Figure 8A:
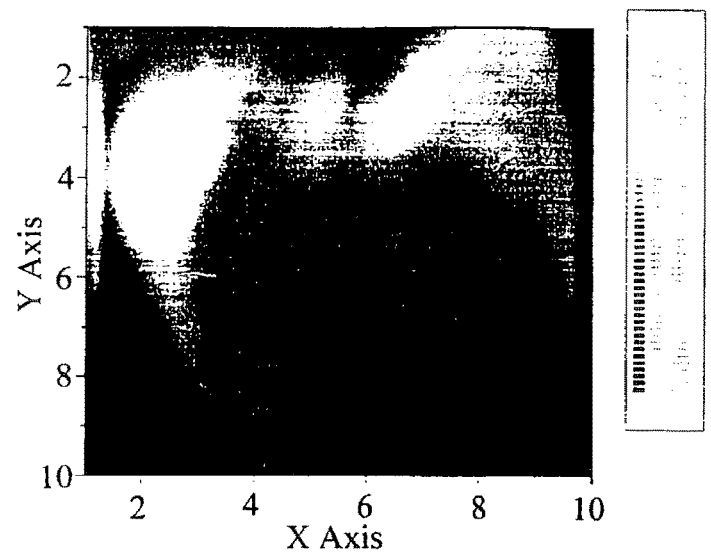
FIGS. 8a and 8b shows two images of a tooth produced using a method in accordance with an embodiment of the present invention.
Figure 8B:
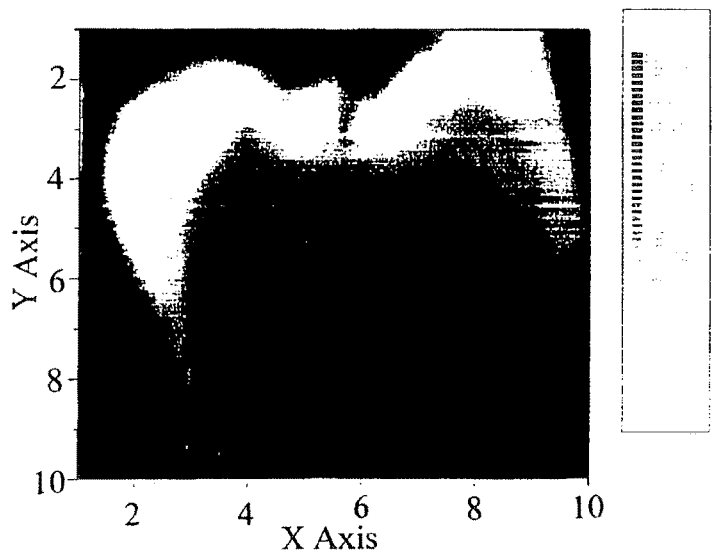

FIGS. 8a and 8b show two images generated using THz radiation of a tooth. FIGS. 8a and 8b were produced in a similar manner to that of FIG. 7. In other words, the image was taken for a single time delay. The time delay chosen was 0 picoseconds for FIG. 8a.

FIG. 8b shows the same tooth of FIG. 8a, however, here the time delay is 6.99 picoseconds. It can be seen that the image in FIG. 8b is far sharper than that of FIG. 8a. The optimum image can be obtained by choosing the correct time delay.

FIG. 9a shows a visible image of a tooth. The tooth is actually a slice through a tooth, the various regions such as the enamel-dentine region 201 and the pulp cavity region 203 can be distinguished. The enamel dentine region 201 has decayed due to caries in regions 205 and 207.

FIG. 9b shows four THz traces plotted as amplitude of detected THz signal against time delay for three regions of the tooth and a reference signal. It can be seen that the reflected detected THz is quite different for the various regions. For example at peak 209, the signal taken in the enamel region (E) of the tooth is seen to dominate. Similarly, at peak 211, the dentine signal (D) is seen to dominate. At peak 213 the signal due to caries (C) dominates the trace. The reference signal (R) is generally seen to be the lowest peak.

By looking at the detected THz signals for different delay times, it is possible to distinguish differences between the different parts of the tooth.

Figure 10A:
Figure 10B:
Figure 10C:
Figure 10D:

FIGS. 9c, 9d and 9e show images of the tooth taken at times −0.08 ps, 0.1 ps and 3.34 ps. These times correspond to the x axis of the FIG. 9b. The trace as seen in FIG. 9b will have to gathered for every part of the tooth of FIG. 10a, but only for a single point on the x-axis, looking at a particular delay time is referred to as taking a time slice through the spectra.

The decayed regions 205 and 207 can be seen in all of FIGS. 9c, 9d and 9e.

FIGS. 10a to 10d show further time slices of the tooth of FIG. 9a, which have not been optimised to illustrate carious regions 205 and 207. Comparing the time slices of FIGS. 10a to 10d with those of FIGS. 9c to 9e, it can be seen that the contrast especially in the caries region 205 and 207 is far more marked in FIGS. 9c to 9e as opposed to FIGS. 10a to 10b.

FIG. 11 shows a range of different images for a tooth. The tooth used to generate the images of FIG. 11 is different to the tooth used to generate the images of FIG. 9. Here, a visible image of a slice through the tooth is shown in FIG. 11a. It can be seen that there is no decay in this tooth. FIG. 11b shows a THz absorption image of the tooth of FIG. 11a. This is just simply obtained by measuring the electric field for each point on the tooth at the detector. The absorption image here is generated from all of the frequencies of the incident pulse of THz radiation, i.e. it is a panchromatic image.

Figure 11A:
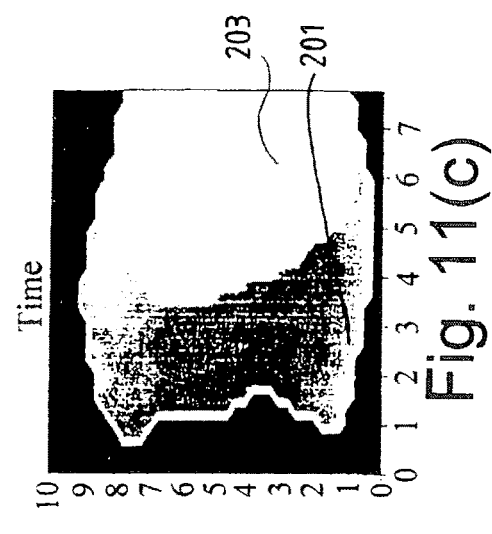
FIG. 11a shows a visible image of a tooth.
Figure 11B:
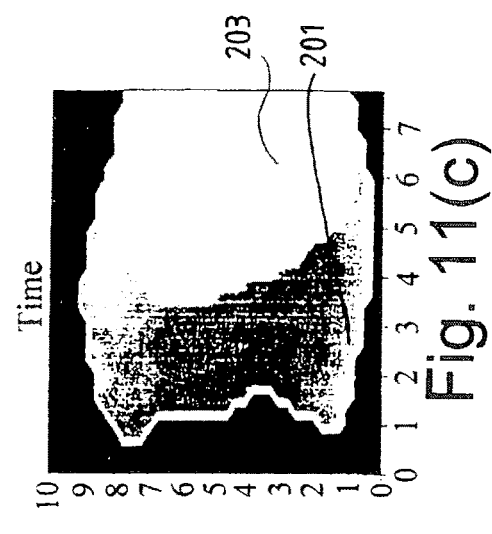
FIG. 11b shows an absorption image of the tooth of FIG. 11a, FIG. 11c shows a time of flight image of the tooth of FIG. 11a, FIGS. 11d to 11f show time slices of the tooth of FIG. 11a for times −0.1 ps, 2.4 ps and 3.1 ps respectively.
Figure 11C:
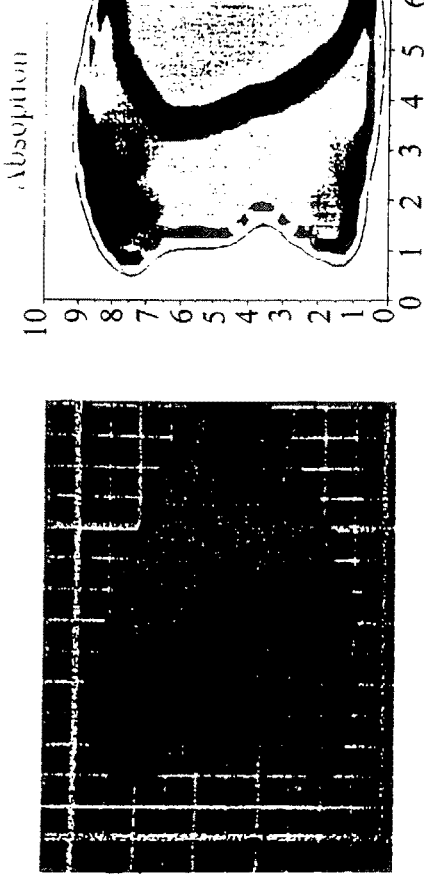

FIG. 11c is a so-called time of flight image. Returning momentarily back to FIG. 9c which shows the THz trace, it can be seen that there is a maxima of the electric field. The time of flight image looks at this maxima and plots the change in temporal position of the this maxima for each point in the area of the sample being imaged.

As with the absorption and visible images, the pulp cavity 203 and the enamel dentine region 201 can be easily distinguished.

Figure 11D:
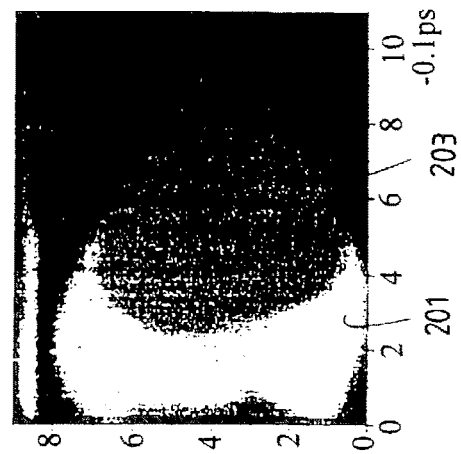
Figure 11E:
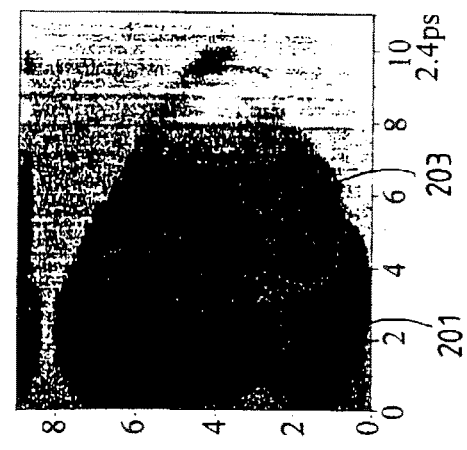
Figure 11F:
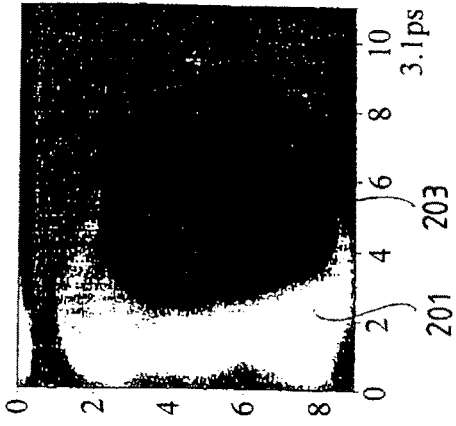

FIGS. 11d, 11e and 11f show time slices (similar to those described for FIGS. 9c to 9Ee) for delay times −0.1 ps, 2.4 ps and 3.1 ps respectively. It can be seen that the contrast of the enamel dentine region 201 with the pulp cavity 203 changes dramatically between the three figures. Also, there is no indication of caries in any of the enamel regions in all of the time slices.

FIG. 12 shows a further tooth. FIG. 12a shows a visible image of the tooth, again the enamel dentine region 201 and the root/pulp cavity 203 can be easily determined. The tooth has a caries region 205 which can not be easily seen on the visible image 203.

Figure 12A:
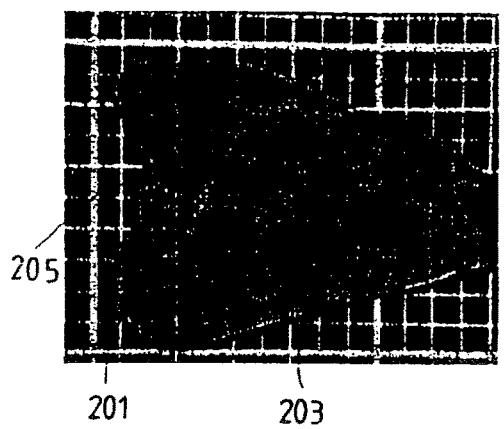
FIG. 12a shows a visible image of a tooth.
Figure 12B:
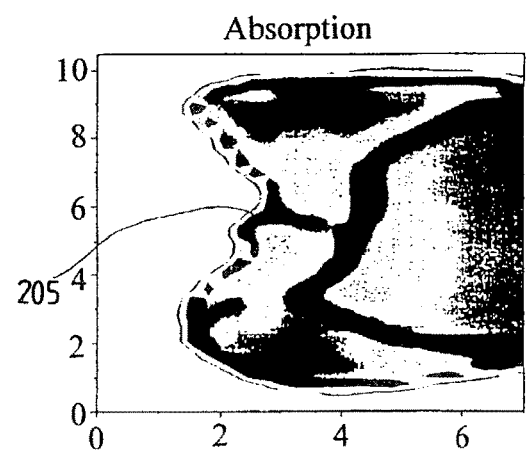
FIG. 12b shows the absorption image of that tooth.

FIG. 12b shows the absorption image which is obtained in the same way as FIG. 11B.

Figure 12C:
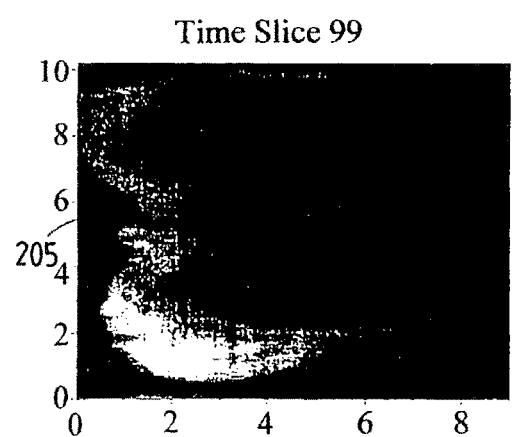
FIG. 12c shows a time slice through that tooth and FIG. 12d shows an image of the tooth plotting the time of the maximum peak of the electric field.
Figure 12D:
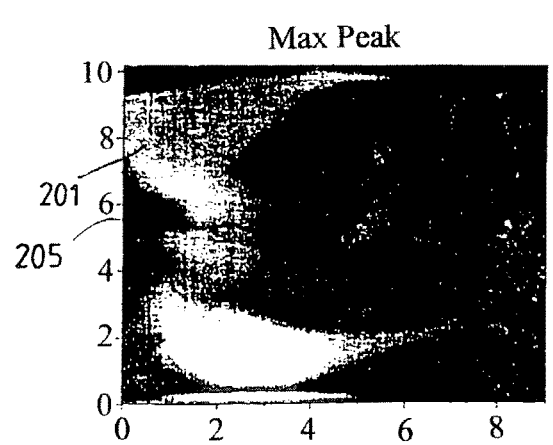

FIG. 12c shows a time slice. In both FIGS. 12c and 12b, the caries region 205 can be easily seen. FIG. 12d shows an image which is plotted by plotting the maxima of the electric field for each point of the sample which is irradiated. The enamel dentine region 201 can be seen. However, the caries region 205 is very weak and much weaker for that than the time slice shown in FIG. 12c. The acquisition time for the time slice can be very fast because it is only necessary to detect the reflected THz for a single point in time.

FIG. 13 shows a further image of a tooth. FIG. 13a shows a visible image whereas FIG. 13b shows a single plot of the THz reflected electric field against time. The THz image is taken along path 101 of the tooth. There are three strong features in the reflected THz. The first peak 103 is due to reflection of the THz from the enamel/air surface. The second peak 105 is due to reflection of the THz from the enamel/dentine interface e-d in the tooth. The third and weakest reflection is due to the dentine/pulp cavity interface d-p of the tooth.

FIG. 14a shows a visible image of a slice of a tooth. The tooth has a healthy region 109 and a decayed region 111. FIG. 14b shows a THz pulse in the time domain measured in the healthy region 109. FIG. 14c shows a THz pulse measured in the time domain for the unhealthy region which is decayed due to caries 111. Returning to the visible image of the tooth slice in FIG. 14a, two interfaces can be seen. The first is the enamel/air interface 113, the second is the enamel/dentine interface 115. In the THz trace, the healthy region two peaks 117 and 119 can be easily distinguished. The upper peak 117 is believed to be due to the reflection of the THz at interface 113, the second peak 119 is due to the reflection of THz at interface 115.

In the THz pulse of the unhealthy region, the peak due to the reflection from interface 113 is seen to be of almost the same height as the corresponding peak in FIG. 14b.

However, the second peak which is due to the reflection from interface 115 is seen to be much smaller. This is because a region of the tooth which is decayed due to caries absorbs THz far more strongly than a region which has not decayed. Hence, less of the THz penetrates as far as interface 115 and THz which is reflected from this interface is also more strongly absorbed than in the case of healthy teeth. Hence, peak 119 is considerably reduced in the trace of the unhealthy region.

Regardless of whether or not the tooth is healthy, the height of the peak from interface 113 should be identical in both traces b and c. However, due to their different positions on the tooth, possibly dirt on the surface of the tooth, they will almost always be different, therefore, in order to detect the presence of caries, the ratio of peak heights 117 and 119 between a healthy region and an unhealthy region should be compared.

This type of analysis does not only apply to teeth. FIG. 15 shows a schematic of a healthy area of skin and an unhealthy area of skin. FIG. 15b shows the THz pulse which has been reflected from a healthy region of the skin, FIG. 15c shows a THz pulse in the time domain which has been reflected from an unhealthy portion of the skin.

Figure 15A:
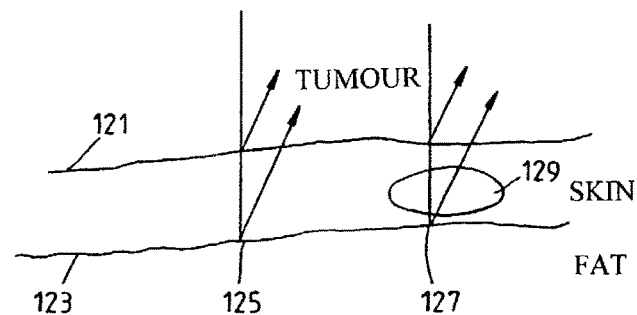
FIG. 15 is a schematic of skin and shows a schematic signal from the skin.
Figure 15B:
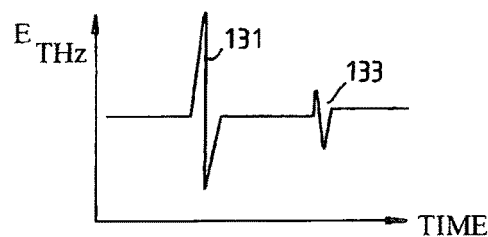
Figure 15C:
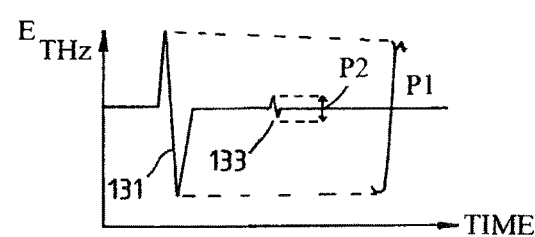

In FIG. 15a, a skin/air interface 121 is shown and a skin/fat interface 123. There is a healthy area 125 and an unhealthy area 127 which contains tumour 129. FIG. 15b shows a THz time domain pulse for the healthy area 125. The first peak 131 is due to reflection from interface 121. The second peak 133 is due to reflection from skin/fat interface 123. FIG. 15c shows a similar trace except here, it is taken in unhealthy region 127. The size of peak 131 remains virtually the same. However, the size of peak 133 is substantially reduced due to the absorption by the tumour 129.

Figure 15D:
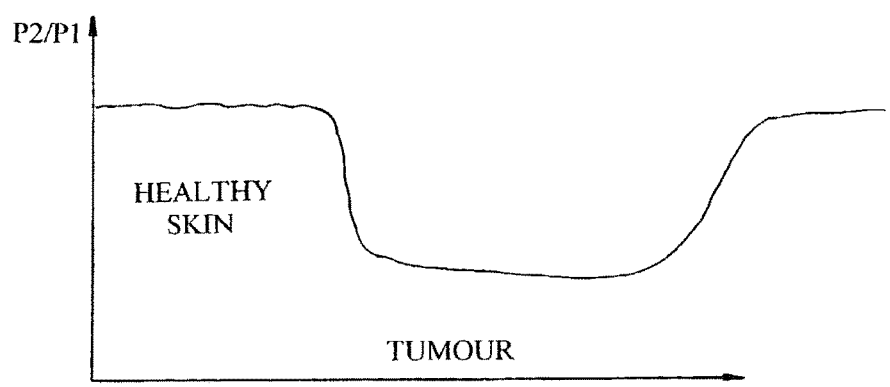

By plotting the ratio of the reflection from the first interface 121 to the second interface 123, across the skin, the lateral extent of the tumour can be determined as shown in FIG. 15d.

It is also possible to obtain information about the depth of a sample using reflection measurement which does not have particularly strongly defined interfaces. Lossy materials, such as biological samples have a relatively large absorption coefficient which dominates how radiation is reflected from the sample.

Figure 16:
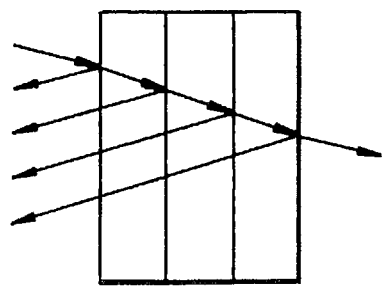
FIG. 16 shows a schematic layer structure of a sample which can be investigated using a method in accordance with an embodiment of the present invention.

FIG. 16, shows a THz pulse incident on a sample. The THz pulse propagates in the x-direction and is scattered (reflected) into a counter-propagating, or reflected, pulse by the object.

To simplify matters, the following analysis will only consider one spatial dimension (x) (i.e. for the case of a collimated THz beam path). It will also be assumed the object is uniform in the y-z plane over the dimensions of the THz beam. Given the 1-D analysis described here to provide information on the structure of the object in the x-direction, the variation of the object in the y-z directions may be obtained by scanning the object through the THz beam in the y-z plane (or, alternatively, scanning the THz beam over the object).

The analysis can be used to determine both how the absorption and the refractive index spatially varies within the sample. In practice, both the absorption coefficient and the refractive index vary also with frequency. The following analysis assumes that the frequency response of the refractive index is known and also that the absorption coefficient does not vary with frequency.

Since the electric field due to the reflected THz pulse may only be measured at discrete points in time, all the integral transforms below must be replaced by the appropriate discrete transform in order to operate on the finite dataset.

The incident and reflected THz pulses are characterised by electric fields T(x,t) and R(x,t) respectively. The quantities in brackets indicate that T and R are both functions of position, x, and time, t. It will be assumed that all electric fields are polarised along a similar axis perpendicular to the x-direction and hence they can be written as scalar quantities (i.e. ignore directional dependence):

$$T(x,t) = \int_{-\infty}^{\infty} T_\omega(x) \cdot e^{-i\omega t} \cdot d\omega$$
$$R(x,t) = \int_{-\infty}^{\infty} R_\omega(x) \cdot e^{-i\omega t} \cdot d\omega$$

where i is the imaginary unit $\sqrt{-1}$. The waves are written in their complex form; the true electric fields are obtained by taking the Real part of the complex waves. $T_\omega$ and $R_\omega$ are the complex amplitudes of the respective incident and reflected waves at each frequency component f where f=2π/ω and these quantities are also functions of position, x. The ω-subscripts indicate that a quantity is a function of ω, k is the wavevector of each frequency component of the wave and is defined by $$k = \frac{n_\omega \omega}{c} + i\frac{\alpha_\omega}{2}$$

where c is the speed of light in a vacuum, $n_\omega$ and $\alpha_\omega$ are the refractive index and absorption coefficients of the object at angular frequency ω. Thus both $n_\omega$ and $\alpha_\omega$ may be functions of position and frequency. These are the materials parameters which characterise the object.

The propagation and coupling of energy between the incident and reflected waves is described by two, coupled $1^{st}$ order differential equations (easily derived from Maxwell's Equations):

$$\frac{\partial T_\omega}{\partial x} + ikT_\omega = \frac{dk}{dx}\frac{1}{2k}R_\omega \qquad \text{Eq. 1}$$
$$\frac{\partial R_\omega}{\partial x} - ikR_\omega = \frac{dk}{dx}\frac{1}{2k}T_\omega$$

The left-hand-sides of the above equations describe the propagation of the two counter-propagating waves. The right-hand-sides provide the 'coupling' terms which transfer energy from one beam to the other in the presence of a scattering potential. In this case, the scattering potential is provided by a spatially varying wave-vector, k. I.e.

$$\frac{dk}{dx}$$

must be non-zero for photons to be transferred from the incident wave to the reflected wave and vice versa. Where $$\frac{dk}{dx} = 0,$$

there is no coupling between the beams and the incident and reflected waves propagate independently.

In a lossy, dispersive medium α≠0 and where $n_\omega$ is frequency dependent.

It will be assumed that the scattering potential is provided by a spatially varying coefficient, Δ(x) such that $$k=k'\Delta$$

$$\frac{1}{k}\frac{dk}{dx} = \frac{d\Delta}{dx}$$

where k' is the spatial average of k and k' is independent of x. (k' remains a function of ω, while Δ is independent of ω).

In order to derive spatial information (i.e. information on how Δ varies with respect to x), it is necessary to know the spectral characteristics of the material in advance (i.e. to know how $n_\omega$ depends on ω). A functional form of $n_\omega(\omega)$ and also the coefficient α are assumed. For the purposes of imaging, this may be calculated from the spatial average THz reflectivity of the sample (i.e. such that structural information is averaged out). The derivation of the spectral characteristics of a sample by THz reflection has been described elsewhere in the literature and will not be reproduced here.

For a lossy medium where α/2>>nω/c (such as water-based biological media) a Real spatial variation in Δ is due to a spatial variation in the absorption coefficient of the medium. Previously, only a spatial variation in the refractive index have been considered.

Furthermore, it is assumed that the spatial variation of k is much smaller than the absolute value of k i.e.

$$\frac{dk}{dx} \ll k,$$

and that the loss of energy from the incident wave due to reflection is much smaller than the loss due to absorption. These conditions are appropriate to most biological samples or sample of high water content. In this approximation, the spatial dependence of the incident wave is independent of the spatial variation of k and is given by $$T_\omega(x) = T_{x=0 \atop \omega} \cdot e^{-ik's}$$

where $T_{x=0}$ is the amplitude of the incident electric field at position x=0 and is a function of $\omega$.

The spatial dependence of the reflected wave may now be described by a single differential equation:

$$\frac{dR_\omega}{dx} - ik'R_\omega = \frac{1}{2}\frac{d\Delta}{dx}T_{x=0 \atop \omega}e^{-ik's} \quad \text{Eq. 2}$$

$$= \left(\frac{1}{2}\frac{d\Delta}{dx}T_{x=0 \atop \omega} \cdot e^{-\frac{\alpha}{2}x}\right)e^{-i\frac{n_\omega \omega}{c}x}$$

$$= T_{x=0 \atop \omega}F(x)e^{-i\frac{n_\omega \omega}{c}x}$$

with $F(x) = \frac{1}{2}\frac{d\Delta}{dx} = e^{-\frac{\alpha}{2}x}$

Equation 2 may be solved (by the method of Laplace transformation, for example), to obtain $R_\omega$:

$$R_\omega(x) = T_{x=0 \atop \omega}\int_{x'=0}^{\infty} F(x') \cdot e^{i\frac{n_\omega \omega}{c}(x-2x')}\,dx'$$

Since it is necessary to measure the reflected wave at one point, we set x=0 to get $$R_{x=0 \atop \omega} = T_{x=0 \atop \omega}\int_{x'=0}^{\infty} F(x') \cdot e^{-i\frac{n_\omega \omega}{c}2x'}\,dx' \quad \text{Eq. 3}$$

This expression may be inverted to obtain F(x) under the assumption that F is independent of $$\left(\frac{n_\omega \omega}{c}\right)$$

This is not strictly true for systems where the absorption is a function of frequency. By making this assumption the analysis is simplified; the effect of the finite frequency dependence of the absorption coefficient is primarily to limit the spatial resolution (in the x-direction) of the final result, at frequencies where the frequency dependence is significant.

By inverse Fourier transformation of Equation 3 we get $$F(x) = \frac{1}{2}\frac{d\Delta}{dx}e^{-\frac{\alpha}{2}x} \approx \frac{1}{2\pi}\int_{-\infty}^{\infty}\frac{R_{x=0 \atop \omega}}{T_{x=0 \atop \omega}}e^{i\frac{2n_\omega \omega}{c}x}\,d\!\left(\frac{2n_\omega \omega}{c}\right) \quad \text{Eq. 4}$$

The spatial dependence of the parameter $\Delta(x)$ contains the structural information about the object which we are trying to deduce. This is obtained by rearranging Equation 4 and integrating over the position, x.

$$\Delta(x) = \quad \text{Eq. 5}$$

$$\frac{1}{2\pi}\int_{x=0}^{\infty} 2e^{-\frac{\alpha}{2}x}\int_{\omega=-\infty}^{\infty}\frac{R_{x=0 \atop \omega}}{T_{x=0 \atop \omega}}e^{i2n_\omega\frac{\omega}{c}}\left(\frac{2n_\omega}{c}+\frac{2\omega}{c}d\frac{n_\omega}{d\omega}\right)\cdot d\omega \cdot dx$$

The factor $R_{x=0,\,\omega}$ is obtained by Fourier transform of the measured reflected THz electric field, R(t) (i.e. as measured at point x=0, corresponding to the surface of the medium or sample):

$$R_{x=0 \atop \omega} = \frac{1}{2\pi}\int_{t=0}^{\infty} R(t)e^{i\omega t}\cdot dt$$

The factor $T_{x=0,\,\omega}$ is obtained by Fourier transform of a reference THz pulse. The THz reference pulse may be obtained by measuring the THz pulse reflected off a sample of known reflectivity such as a silver mirror, for example. The THz pulse reflected from a silver mirror is an exact replica of the incident THz pulse i.e.

$$T^{silver}(t)=R^{silver}(t)$$

A similar transformation is performed on T(t):

$$T_{x=0 \atop \omega} = \frac{1}{2\pi}\int_{t=0}^{\infty} T(t)e^{i\omega t}\cdot dt$$

In practice, the incident THz pulse must have a finite bandwidth; that is, $T_{x=0,\,\omega}$ will drop below the noise-level of the measurement apparatus at frequencies above some threshold, $\omega_{max}$. Similarly, $T_{x=0,\,\omega}$ will drop below the measurement noise at frequencies below some minimum threshold, $\omega_{min}$. In order to exclude artefacts due to noise where $T_{x=0,\,\omega}$ has become small, we included a windowing function $W(\omega)$. This function has the property that it drops to zero at both high and low frequencies faster than $T_{x=0,\,\omega}$.

For example, we may choose $W_\omega = W(\omega)$ to be a square-pulse function:

$$\left\{\begin{array}{l} W(\omega)=1;\ \omega_{min}<\omega<\omega_{max} \\ W(\omega)=0;\ \text{all other } \omega \end{array}\right\}$$

The final result is $$\Delta(x) = \quad \text{Eq. 6}$$

$$\frac{1}{2\pi}\int_{x=0}^{\infty} 2e^{\frac{\alpha}{2}x}\int_{\omega=-\infty}^{\infty}\frac{R_{x=0 \atop \omega}}{T_{x=0 \atop \omega}}W_\omega e^{i2n_\omega\frac{\omega}{c}}\left(\frac{2n_\omega}{c}+\frac{2\omega}{c}\frac{dn_\omega}{d\omega}\right)\cdot d\omega \cdot dx$$

$$\frac{dn_\omega}{d\omega}$$

may be calculated directly from the previously determined functional form of $n_\omega$.

Equation 6 constitutes the main result. $\Delta(x)$ is obtained by numerical evaluation of Equation 6, once all the constituent factors have been determined. Since $\Delta$ is complex either the real or the imaginary part of the function may be plotted to form an image, or some combination. A obtained in this way is considered only an approximation to the exact structural form of the sample, in view of the approximations described above.

Figure 17:
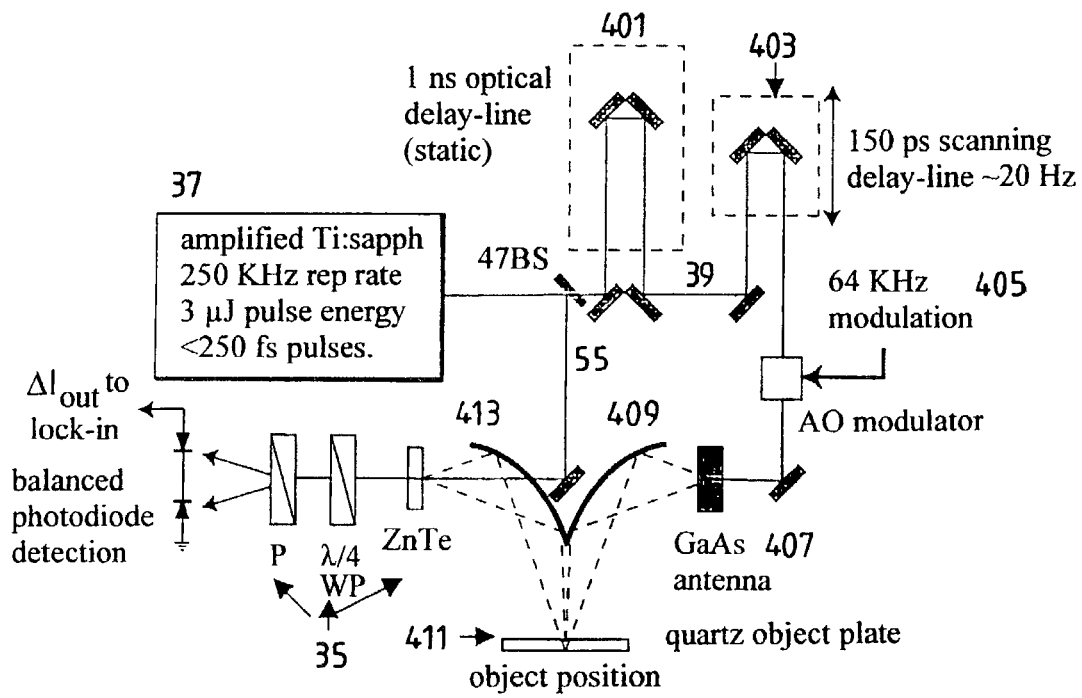
FIG. 17 shows a schematic of a variation of the imaging system of FIG. 1.

FIG. 17 shows an imaging system which is similar to FIG. 1. To avoid unnecessary repetition, like reference numerals will be used to denote like features. A Ti:Sapphire laser system 37 (coherent Reg A9000) operating at a 250 kHz repetition rate is used to provide the input radiation. The radiation is split using beam splitter 47 to produce a probe beam 55 and a pump beam 39. The pump beam is first directed through a 1 ns delay line 401. This is a static delay line and is used to make fine adjustments to the path length. The pump beam is then directed into a 150 ps scanning delay line 403 having a scanning frequency of 20 Hz. The scanning delay line has a linear-position output so that it is possible to know the position of the delay line when each measurement is taken. The pump beam is then fed through a 64 kHz modulator 405 which chops the beam at this frequency in order to provide a frequency for detection using lock-in techniques.

The pump beam 39 is then directed onto GaAs antenna 407. The antenna is biased to 1.1 kV and average powers of over 1 nW are generator. The pump beam 39 power delivered to the antenna is 1 to 2 µJ. Such antennas are described in detail in J. T. Darrow and B. B. Hu and X.-C. Zhang and D. H. Auston 1990, *Optics Lett.*, 15(6), pages 323-5, Z. G. Lu and P. Campbell and X.-C. Zhang, 1997 *Appl. Phys. Lett.*, 71(5), pages 593-5, and G. Mouret and W. Chen and D. Boucher and R. Bocquet and P Mounaix and D. Theron and D. Lippens, 1998, *Microwave and optical technol. lett.*, 17(1), pages 23-7. In the specific antenna of this example, an acrylic anti-corona coating is used and a 100 KΩ series resistor to suppress dielectric breakdown of the device and to reduce power-dissipation in the GaAs. The emitted THz pulses are guided from antenna 407 via off-axis parabolic mirror 409 onto sample 411. The reflected radiation from the sample is then collected via parabolic mirror 413 and directed into detector 35. The detector is of the EOS type described with reference to FIG. 3. In the specific example of FIG. 17, the reflected THz beam is directed onto 1 mm thick ZnTe crystal colinearly with the probe beam 55.

Where non-planar soft materials, for example, human skin are measured, a quartz window is used in order to flatten the skin to improve the image.

Figures 18A, 18B:
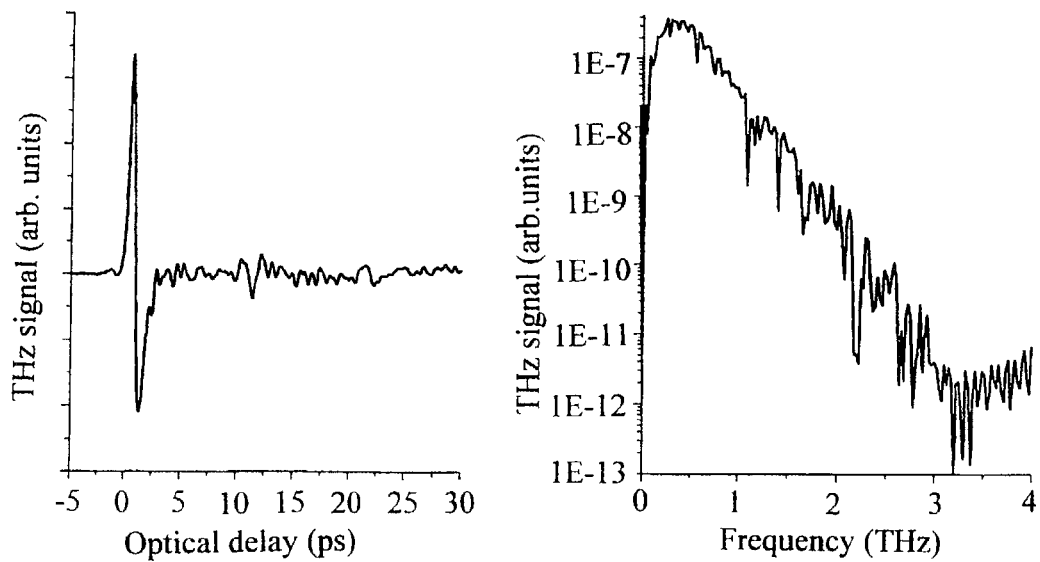
FIG. 18a shows a typical signal measured by the apparatus of FIG. 17
FIG. 18b shows the corresponding THz power spectrum.

FIG. 18a shows a typical plot of THz signal (arbitrary units) against delay time of the optical pulse (measured by the 150 ps scanning delay line) which can be obtained using the apparatus of FIG. 17. The smaller oscillations after the main pulse are due to atmospheric water-vapour absorption and dispersion in the THz beam path. A small signal can be seen at 10 ps after the main pulse due to back-reflections from the GaAs antenna substrate. The signal-to-noise ratio for a typical THz waveform (measured with a metallic mirror in place of a sample) is greater than 6000 to 1 for a single delay line scan. This typically has an acquisition time of 50 ms.

The bandwidth envelope which is obtained from Fourier transforming the time domain waveform of FIG. 18a is shown in FIG. 18b. FIG. 18b actually shows the THz power spectrum. The spectrum peaks at 300 GHz with useful power to over 3 THz. The large THz throughput of the system allows the acquisition time for 3D data sets to be reduced to just a few minutes.

Figure 19:
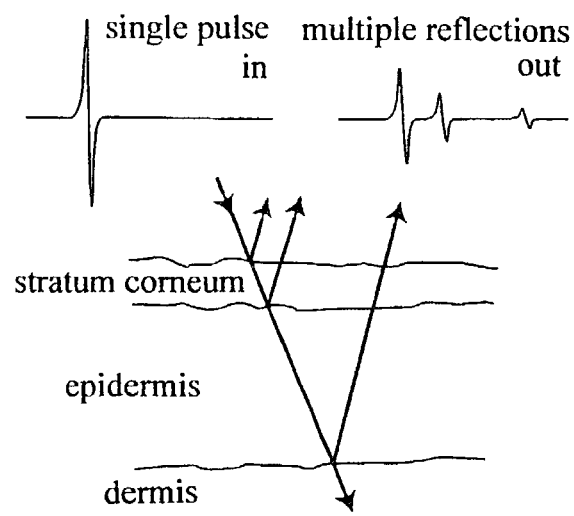
FIG. 19 shows a schematic of the layers of skin and an input and reflected pulses.

FIG. 19 is a schematic of the outermost layers of human skin. The stratum corneum 421 being the outermost layer, the middle layer is the epidermis 423 and the innermost layer of interest in these experiments is the dermis layer 425. When a single THz pulse 427 is reflected from the skin, multiple reflections due to the stratum corneum/air interface 429, stratum corneum/epidermis interface 431 and the epidermis/dermis interface 433. The signal from each of these interfaces can be seen in the output pulse 435.

The data shown in FIGS. 20 to 25 is taken from the human arm shown in FIG. 20. Point a indicates the centre inside forum, point b indicates the inside wrist, point c indicates the palm of the hand, point d indicates the side of the hand and point e indicates the second fingertip. THz radiation is non-ionising and low average powers are used (typically 1 mW). Therefore, brief exposure to it is not thought to be hazardous.

Figure 21A:
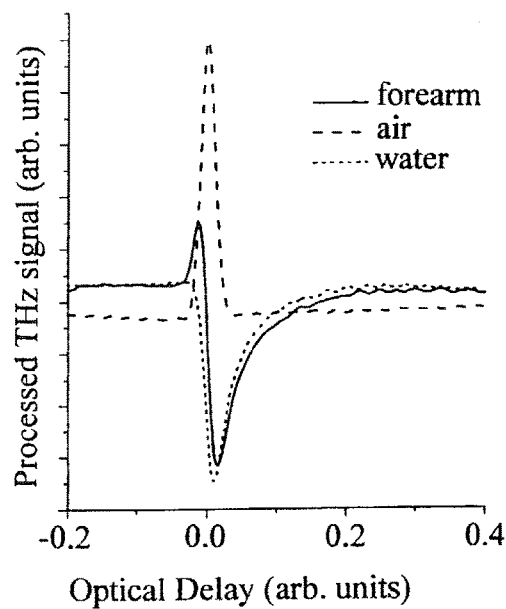
FIG. 21a is a plot of a time domain THz waveform measured from the forearm and compared with that from air and water.

FIG. 21a shows a time domain THz waveform obtained from point a on FIG. 20. The time domain waveform has been processed in order to remove some unwanted artefacts. The oscillations following the main pulse due to atmospheric water removed by deconvolving the data set with the reference pulse waveform obtained in the absence of the sample. The data set is also spectrally filtered to remove out of band noise by applying a band pass filter with pass band adjusted to match that of the reference pulse.

In FIG. 21a, the data for point a is shown as a solid line. This is compared with a dashed line which shows data for air (measured in absence of sample) and a dotted line which shows the waveform obtained from a pure water sample.

The THz waveform in the absence of the sample (dashed line) shows a gaussian pulse corresponding to reflection from the top surface of the window (window-air interface). The width of this gaussian indicates the temporal resolution obtainable with the technology as determined by the band width of the THz pulse.

The waveform obtained from water is opposite in polarity to the no-sample case as expected for a reflection from a higher refractive-index dielectric. After the initial transient, water displays a damped decay back to zero over a period of 1 to 2 ps.

The THz waveform of the forearm from point a displays a positive peak at zero optical delay corresponding to the presence of the relatively dehydrated stratum corneum layer. For delay values greater than this, the THz waveform appears to be substantially similar to that for water. This indicates that there is a high water content in the upper dermal layer. The bandwidth of the system is efficient to a depth resolution of about 40 µm into the skin. The stratum corneum of the forearm is typically 10 to 20 µm. The positive peak can be taken as a measure of the dehydration volume of the stratum corneum. The stratum corneum thickness cannot be distinguished from the dehydration level in this case.

Figure 21B:
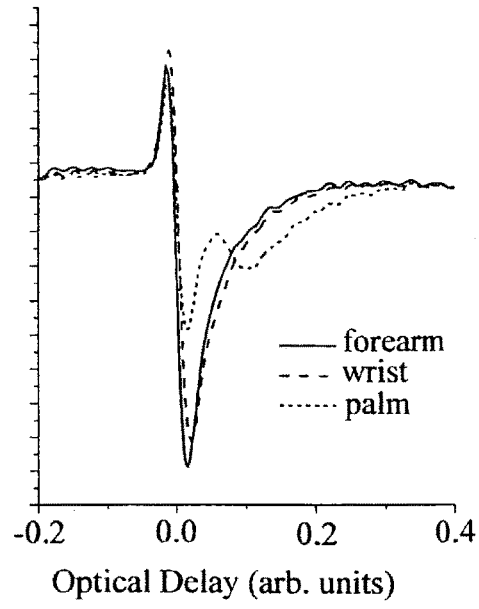
FIG. 21b is a THz waveform comparing the reflected pulse from the forearm, wrist and palm.

FIG. 21b shows a process waveform for skin at point a (solid line), point b (dashed line) and point c (dotted line). There is little reproducible difference between the scans for the forearm and the wrist. However, the palm gives significantly different results. In this case, there is a differential feature due to reflection of the stratum corium surface followed, at a longer delay time by a broader negative transient due to the stratum corneum-epidermis interface. This transient displays the damp decay to zero expected for the water-like epidermis. The stratum corneum has a thickness from 100 to 150 µm on the palm of the hand which is thick enough for its inner and outer boundaries to be separated.

Figure 22A:
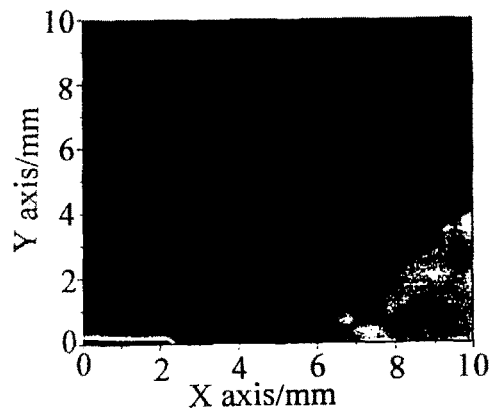
FIG. 22a is a 1 cm by 1 cm image of the side of the hand of FIG. 20.

FIGS. 22a and b show images obtained by raster scanning a 1 cm by 1 cm area of the side of the subject's hand (point d) in FIG. 20.

Figure 22B:
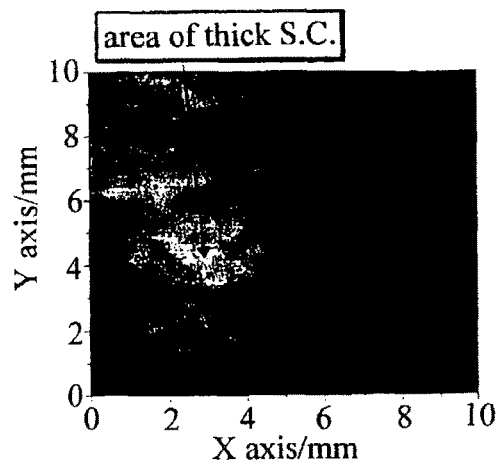
FIG. 22b is a time slice image of the hand.

FIG. 22a is generated by plotting the peak value of the processed THz waveform corresponding to the outside surface of the stratum corneum along the z axis (i.e. out of the palm) across the whole 1 cm by 1 cm area). Typical features of the skin surface (lines, wrinkles etc) are evident. FIG. 22b shows essentially a time slice image where the THz waveform values at a time delay corresponding to the stratum corneum-epidermis interface are plotted. This allows variations in the stratum corneum thickness over the scanned area to be seen. (Low x values are towards the palm side of the hand while the higher values are towards the back-side).

Figure 23A:
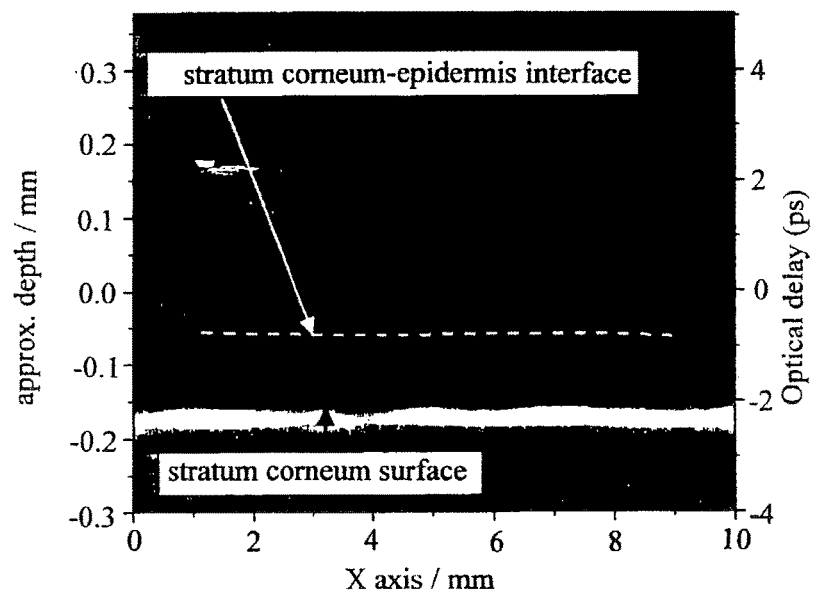
FIG. 23a is an image of the palm of the hand of FIG. 20.
Figure 23B:
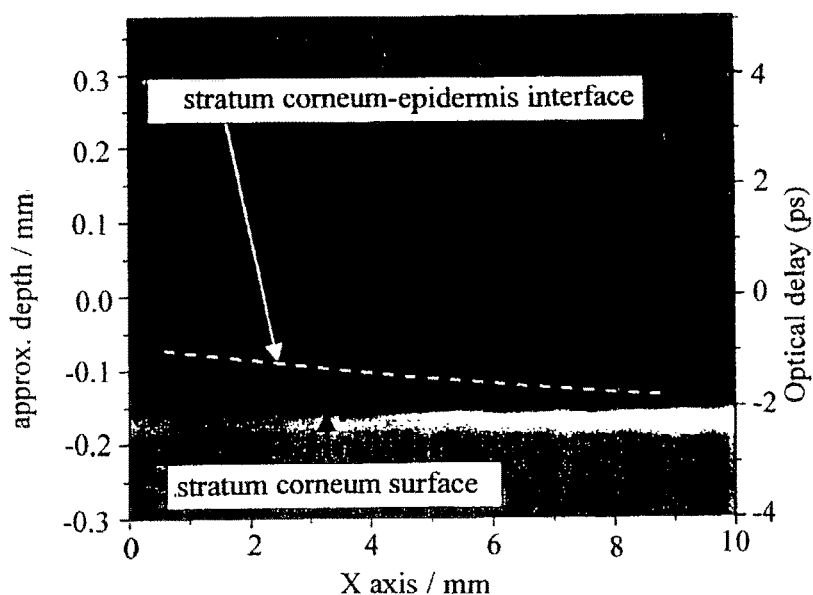
FIG. 23b shows the corresponding data from the edge of the subject's palm.

In the data of both FIG. 22a and FIG. 22b, the reflected THz waveforms are acquired over a spatial interval of 3 waveforms per millimeter along the two axis. This is roughly equivalent to the diffraction limited resolution achievable in this frequency regime. FIGS. 23a and 23b show slices through a 3D data set. The grey scale indicates the THz amplitude and is plotted against optical delay (vertical access) and x position across the horizontal axis. A depth calibration is obtained from the optical delay time based on an assumed refractive index of n=2 for skin tissues over the THz regime. The figures indicate the stratum corneum/epidermis interface and also the stratum corneum surface. FIG. 23a is taken at point c whereas FIG. 23b is taken at point d.

The sensitivity of THz towards absorption is shown in FIG. 24a. Here, the reflective parts from the forearm of FIG. 20 were measured before and at intervals after hydrating the stratum corneum by application of water-soaked gauze. Trace "a" shows a THz signal prior to removal of the gauze, trace "b" shows the signal immediately after removal of the gauze. Here, it can be seen that the THz waveform is strongly suppressed at zero optical delay indicating near-saturated hydration of the stratum corneum and traces "c" to "e" show the same measurement five minutes, ten minutes and fifteen minutes respectively after removal of the gauze. The soaked region of skin is exposed to an ambient atmosphere (23° C.). The zero-delay peak covers over a characteristic time of 15 minutes. It is interesting to note that although the positive peak covers after initial hydration, the following minimum is first reduced in depth by hydration and subsequently increases to become more negative than before hydration.

FIG. 24b shows the change in the hydration level of the stratum corium produced by application of 60 milligrams of 10% glycerine solution. The dotted line indicates the waveform before the glycerine is applied. The solid line shows the waveform 8 minutes after application of the solution. The upper trace for point "c" (palm) whereas the lower trace is for point "a" (forearm).

The forearm for glycerine results display the same suppression of the zero-delay peak as those achieved using pure water. Actually, the zero-delay peak appears more strongly suppressed than in the pure water case after five minutes drying time. Indicating the improved retention of water in the presence of glycerine. Little change is seen in the hydration level of the palm. However, small changes in the features of a later time delay can be seen.

FIG. 25a illustrates the effect of occlusion of the stratum corneum interface by the quartz window. Here, THz measurements were made at 45 second intervals over a 15 minute period with the skin in continuous contact with quartz. The scans are offset from one another along the x axis with the later most times to the right. The size of the zero-delay peak decreases with an exponential decay form.

The peak-to-peak values for each waveform is plotted as a function of time in FIG. 25b. An exponential decay is fitted to the data. It was found that the time-constant for the decay is 3.1 minutes.

The invention claimed is:

1. A method of imaging a sample, the method comprising:
   irradiating a plurality of points of a surface of the sample with a pulse of electromagnetic radiation, said pulse having a plurality of frequencies in the range from 25 GHz to 100 THz;
   detecting the amplitude of the radiation having a plurality of frequencies in the range from 25 GHz to 100 THz reflected from or transmitted by each point of the sample as a function of delay time, wherein the delay time is the time that it takes the radiation to travel through a region of the sample;
   generating a first two-dimensional image of the points of the sample at a first interface of the sample using an amplitude of the radiation detected for a delay time corresponding to the first interface; and
   generating a second two-dimensional image of the points of the sample at a second interface of the sample using an amplitude of the radiation detected for a delay time corresponding to the second interface;
   obtaining a depth calibration based on a refractive index;
   determining variation in thickness of the layer of the sample between the first interface and the second interface from the delay time corresponding to the first interface and the delay time corresponding to the second interface.

2. A method according to claim 1, wherein the first interface is an internal dielectric interface or an external surface of the sample and the second interface is an internal dielectric interface or an external surface of the sample.

3. A method according to claim 2, wherein the first interface is a first external surface of the sample and the second interface is a second external surface of the sample and determining the variation in thickness of the layer of the sample between the first interface and the second interface comprises determining the variation in the depth of the sample.

4. An apparatus for generating an image of a sample, the apparatus comprising:
   an emitter for irradiating a plurality of points of a surface of a sample with a pulse of electromagnetic radiation, said pulse having a plurality of frequencies in the range from 25 GHz to 100 THz;
   a detector for detecting the amplitude of the radiation having a plurality of frequencies in the range from 25 GHz to 100 THz reflected from or transmitted by each point of the sample as a function of delay time wherein the delay time is the time that it takes radiation to travel through a region of the sample; and
   a processor:
      for generating a first two dimensional image of the points of the sample at a first interface of the sample using an amplitude of the radiation detected for a delay time corresponding to the first interface;
      for generating a second two dimensional image of the points of the sample at a second interface of the sample using an amplitude of the radiation detected for a delay time corresponding to the second interface; and
      for obtaining a depth calibration based on a refractive index and determining variation in thickness of the layer of the sample between the first interface and the second interface, from the delay time corresponding to the first interface and the delay time corresponding to the second interface.

5. An apparatus according to claim 4, wherein the first interface is an internal dielectric interface or an external surface of the sample and the second interface is an internal dielectric interface or an external surface of the sample.

6. A method according to claim 1, wherein the delay time is measured by varying the phase of a reference beam with respect to the beam of reflected radiation.

7. A method according to claim 1, wherein one of the first image and the second image show features of the sample surface.

* * * * *